(12) United States Patent  (10) Patent No.: US 9,349,303 B2
Freeman  (45) Date of Patent: *May 24, 2016

(54) AUTOMATED CAREGIVING DEVICE WITH PROMPTING BASED ON CAREGIVER PROGRESS

(71) Applicant: ZOLL Medical Corporation, Chelmsford, MA (US)

(72) Inventor: Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/275,860

(22) Filed: May 12, 2014

(65) Prior Publication Data

US 2015/0031961 A1  Jan. 29, 2015

Related U.S. Application Data

(63) Continuation of application No. 13/477,335, filed on May 22, 2012, now Pat. No. 8,725,254, which is a continuation of application No. 12/721,874, filed on Mar. 11, 2010, now Pat. No. 8,204,589, which is a continuation of application No. 10/841,367, filed on May 7, 2004, now Pat. No. 7,706,878.

(51) Int. Cl.
| | |
|---|---|
| *A61N 1/38* | (2006.01) |
| *G09B 23/28* | (2006.01) |
| *A61B 5/00* | (2006.01) |
| *A61N 1/39* | (2006.01) |
| *G09B 5/06* | (2006.01) |

(52) U.S. Cl.
CPC ............ *G09B 23/288* (2013.01); *A61B 5/4848* (2013.01); *A61N 1/3987* (2013.01); *G09B 5/06* (2013.01)

(58) Field of Classification Search
None
See application file for complete search history.

(56) References Cited

U.S. PATENT DOCUMENTS

| | | |
|---|---|---|
| 4,019,501 A | 4/1977 | Harris |
| 4,077,400 A | 3/1978 | Harrigan |
| 4,095,590 A | 6/1978 | Harrigan |
| 4,588,383 A | 5/1986 | Parker et al. |

(Continued)

FOREIGN PATENT DOCUMENTS

| | | |
|---|---|---|
| JP | 2000-176025 | 6/2000 |
| JP | 2002-514107 | 5/2002 |

(Continued)

OTHER PUBLICATIONS

Cummins et al., Defibrillator Failures: Causes and Problems and Recommendations for Improvement, JAMA, vol. 264, No. 8 (1990).

(Continued)

*Primary Examiner* — Brian T Gedeon
(74) *Attorney, Agent, or Firm* — Fish & Richardson P.C.

(57) ABSTRACT

A device for assisting a caregiver in delivering therapy to a patient, the device comprising a user interface configured to deliver prompts to a caregiver to assist the caregiver in delivering therapy to a patient; at least one sensor configured to detect the caregiver's progress in delivering the therapy, wherein the sensor is other than an electrode in an electrical contact with the body; a memory in which a plurality of different prompts are stored; a processor configured to determine which of the different prompts should be selected for delivery based on the progress detected by the sensor.

19 Claims, 21 Drawing Sheets

(56) References Cited

U.S. PATENT DOCUMENTS

| | | | |
|---|---|---|---|
| 4,610,254 | A | 9/1986 | Morgan et al. |
| 4,863,385 | A | 9/1989 | Pierce |
| 5,137,458 | A | 8/1992 | Ungs et al. |
| 5,285,792 | A | 2/1994 | Sjoquist et al. |
| 5,496,257 | A | 3/1996 | Kelly |
| 5,662,690 | A | 9/1997 | Cole et al. |
| 5,700,281 | A | 12/1997 | Brewer et al. |
| 5,792,190 | A | 8/1998 | Olson et al. |
| 5,853,292 | A | 12/1998 | Eggert et al. |
| 5,913,685 | A | 6/1999 | Hutchins |
| 5,955,956 | A | 9/1999 | Stendahl et al. |
| 6,125,299 | A | 9/2000 | Groenke et al. |
| 6,306,107 | B1 | 10/2001 | Myklebust et al. |
| 6,334,070 | B1 | 12/2001 | Nova et al. |
| 6,356,785 | B1 | 3/2002 | Snyder et al. |
| 6,370,428 | B1 | 4/2002 | Snyder et al. |
| 6,390,996 | B1 | 5/2002 | Halperin et al. |
| 6,405,082 | B1 | 6/2002 | Borgenicht |
| 6,697,671 | B1 | 2/2004 | Nova et al. |
| 6,827,695 | B2 | 12/2004 | Palazzolo et al. |
| RE40,471 | E | 8/2008 | Groenke et al. |
| 7,706,878 | B2 | 4/2010 | Freeman |
| 7,729,757 | B2 | 6/2010 | Parascandola et al. |
| 2002/0007832 | A1 | 1/2002 | Doherty |
| 2003/0004547 | A1 | 1/2003 | Owen et al. |
| 2003/0036044 | A1 | 2/2003 | Pastrick et al. |
| 2003/0055458 | A1 | 3/2003 | Hamilton et al. |
| 2003/0083699 | A1 | 5/2003 | Hamilton et al. |
| 2003/0216785 | A1 | 11/2003 | Edwards et al. |
| 2005/0070964 | A1 | 3/2005 | Hansen et al. |

FOREIGN PATENT DOCUMENTS

| | | |
|---|---|---|
| JP | 2002-360711 | 12/2002 |
| JP | 2003-525712 | 9/2003 |
| WO | 03/024521 | 3/2003 |

OTHER PUBLICATIONS

Part 4: The Automated External Defibrillator: Key Link in the Chain of Survival, Circulation 102:60-76 (2000).

| PROMPT # | PROMPT |
|---|---|
| 1 | CHECK RESPONSIVENESS, SHOUT ARE YOU OK, |
| 2 | IF UNRESPONSIVE, SHOUT HELP LOUDLY |
| 3 | CALLING 911 |
| 4 | FOLLOW LIT PICTURES |
| 5 | LOOK CAREFULLY AT THE PICTURE SHOWN ON THE COVER. |
| 6 | PLACE PERSON ON THEIR BACK WITH THE COVER UNDERNEATH THE SHOULDERS AS SHOWN IN THE PICTURE. |
| 7 | THE COVER IS UPSIDE DOWN. PLEASE PLACE THE COVER WITH THE INSTRUCTION LABEL FACING YOU. |
| 8 | PLACE THE VICTIM'S SHOULDERS DIRECTLY ON THE COVER AS SHOWN ON THE INSTRUCTION LABEL. |
| 9 | TILT HEAD AND LIFT CHIN AS SHOWN IN THE LIT PICTURE TO OPEN THE PERSON'S AIRWAY. |
| 10 | KNEEL BESIDE THE PERSON'S RIGHT SHOULDER. CHECK BREATHING BY PLACING YOUR EAR OVER THE VICTIM'S NOSE AND MOUTH WHILE MAINTAINING AN OPEN AIRWAY. |
| 11 | LOOK FOR THE CHEST TO RISE AND FALL, LISTEN FOR AIR ESCAPING WHILE BREATHING, AND FEEL FOR THE FLOW OF AIR. |
| 12 | IF NOT BREATHING THEN TILT HEAD, LIFT CHIN, AND PINCH NOSE AS SHOWN IN LIT PICTURE AND GIVE VICTIM TWO BREATHS |
| 13 | MAKE SURE TO BREATHE MORE DEEPLY INTO PATIENT. |
| 14 | CHECK PULSE. PLACE FINGERS AS SHOWN IN LIT PICTURE AT THE SIDE OF THE NECK. |
| 15 | PRESS GENTLY TO FEEL FOR PULSE. |
| 16 | IF NO DETECTED PULSE, THE PERSON IS PROBABLY IN CARDIAC ARREST. |
| 17 | REMOVE CLOTHING FROM VICTIM'S CHEST |
| 18 | OPEN WHITE ELECTRODE PACKAGE |
| 19 | LOOK CAREFULLY AT PICTURE ABOVE RED CROSS |
| 20 | LOOK CAREFULLY AT PICTURE BESIDE RED ARROW TAB # 2 |
| 21 | PLACE RIGHT HAND ON RED CROSS |

FIG. 7A

| PROMPT # | PROMPT |
|---|---|
| 22 | PULL RED ARROW TAB # 2 (TO REMOVE WHITE PLASTIC) AS SHOWN IN PICTURE |
| 23 | THE BLUE BACKING STILL SEEMS TO BE ATTACHED TO THE WHITE PAD. YOU NEED TO REMOVE IT BEFORE YOU ATTACH THE ELECTRODES TO THE PATIENT. |
| 24 | PLEASE MAKE SURE THAT THERE ISN'T ANY CLOTHING UNDERNEATH THE WHITE FOAM PADS YOU PLACED ON THE VICTIM'S CHEST. |
| 25 | PRESS PAD FIRMLY TO VICTIM'S BARE CHEST |
| 26 | LOOK CAREFULLY AT PICTURE BESIDE RED ARROW TAB # 3 |
| 27 | PLACE LEFT HAND ON RED CROSS |
| 28 | PULL RED ARROW TAB # 3 (TO REMOVE WHITE PLASTIC) AS SHOWN IN PICTURE |
| 29 | GRAB RED PULL TAB ON THE CORNER OF THE WHITE PACKAGE AND PULL FIRMLY TO TEAR OPEN PACKAGE. IF UNABLE TO TEAR OPEN, CUT ALONG DOTTED LINE WITH SCISSORS. |
| 30 | PRESS PAD FIRMLY TO VICTIM'S BARE CHEST |
| 31 | PRESS FLASHING HEART |
| 32 | IF NO CIRCULATION PLACE HANDS ON RED CROSS AS INDICATED BY LIT PICTURE |
| 33 | PRESS DOWN HARD 15 TIMES THEN GIVE TWO BREATHS |
| 34 | PUSH FASTER |
| 35 | PUSH HARDER |

FIG. 7B

AUTOMATED CAREGIVING DEVICE WITH PROMPTING BASED ON CAREGIVER PROGRESS

CROSS-REFERENCE TO RELATED APPLICATIONS

This application is a continuation application of and claims priority to U.S. application Ser. No. 13/477,335, filed on May 22, 2012, which application is a continuation application of and claims priority to U.S. application Ser. No. 12/721,874, filed on Mar. 11, 2010, now issued U.S. Pat. No. 8,204,589, which application is a continuation application of and claims priority to U.S. application Ser. No. 10/841,367, filed on May 7, 2004, now U.S. Pat. No. 7,706,878. These applications are hereby incorporated by reference.

TECHNICAL FIELD

This invention relates to devices for assisting caregivers in delivering therapy to a patient (e.g., automatic external defibrillators).

BACKGROUND

Resuscitation treatments for patients suffering from cardiac arrest generally include clearing and opening the patient's airway, providing rescue breathing for the patient, and applying chest compressions to provide blood flow to the victim's heart, brain and other vital organs. If the patient has a shockable heart rhythm, resuscitation also may include defibrillation therapy. The term basic life support (BLS) involves all the following elements: initial assessment; airway maintenance; expired air ventilation (rescue breathing); and chest compression. When all these elements are combined, the term cardiopulmonary resuscitation (CPR) is used.

There are many different kinds of abnormal heart rhythms, some of which can be treated by defibrillation therapy ("shockable rhythms") and some which cannot (non-shockable rhythms"). For example, most ECG rhythms that produce significant cardiac output are considered non-shockable (examples include normal sinus rhythms, certain bradycardias, and sinus tachycardias). There are also several abnormal ECG rhythms that do not result in significant cardiac output but are still considered non-shockable, since defibrillation treatment is usually ineffective under these conditions. Examples of these non-shockable rhythms include asystole, electromechanical disassociation, and other pulseless electrical activity. Although a patient cannot remain alive with these non-viable, non-shockable rhythms, applying shocks will not help convert the rhythm. The primary examples of shockable rhythms, for which the caregiver should perform defibrillation, include ventricular fibrillation, ventricular tachycardia, and ventricular flutter.

After using a defibrillator to apply one or more shocks to a patient who has a shockable ECG rhythm, the patient may nevertheless remain unconscious, in a shockable or non-shockable, perfusing or non-perfusing rhythm. If a non-perfusing rhythm is present, the caregiver may then resort to performing CPR for a period of time in order to provide continuing blood flow and oxygen to the patient's heart, brain and other vital organs. If a shockable rhythm continues to exist or develops during the delivery of CPR, further defibrillation attempts may be undertaken following this period of cardiopulmonary resuscitation. As long as the patient remains unconscious and without effective circulation, the caregiver can alternate between use of the defibrillator (for analyzing the electrical rhythm and possibly applying a shock) and performing cardio-pulmonary resuscitation (CPR). CPR generally involves a repeating pattern of five or fifteen chest compressions followed by a pause during which two rescue breaths are given.

Defibrillation can be performed using an AED. The American Heart Association, European Resuscitation Council, and other similar agencies provide protocols for the treatment of victims of cardiac arrest that include the use of AEDs. These protocols define a sequence of steps to be followed in accessing the victim's condition and determining the appropriate treatments to be delivered during resuscitation. Caregivers who may be required to use an AED are trained to follow these protocols.

Most automatic external defibrillators are actually semi-automatic external defibrillators (SAEDs), which require the caregiver to press a start or analyze button, after which the defibrillator analyzes the patient's ECG rhythm and advises the caregiver to provide a shock to the patient if the electrical rhythm is shockable. The caregiver is then responsible for pressing a control button to deliver the shock. Following shock delivery, the SAED may reanalyze the patient's ECG rhythm, automatically or manually, and advise additional shocks or instruct the caregiver to check the patient for signs of circulation (indicating that the defibrillation treatment was successful or that the rhythm is non-shockable) and to begin CPR if circulation has not been restored by the defibrillation attempts. Fully automatic external defibrillators, on the other hand, do not wait for user intervention before applying defibrillation shocks. As used below, automatic external defibrillators (AED) include semi-automatic external defibrillators (SAED).

Both types of defibrillators typically provide an auditory "stand clear" warning before beginning ECG analysis and/or the application of each shock. The caregiver is then expected to stand clear of the patient (i.e., stop any physical contact with the patient) and may be required to press a button to deliver the shock. The controls for automatic external defibrillators are typically located on a resuscitation device housing.

AEDs are typically used by trained medical or paramedic caregivers, such as physicians, nurses, emergency medical technicians, fire department personnel, and police officers. The ready availability of on-site AEDs and caregivers trained to operate them is important because a patient's chances of survival from cardiac arrest decrease by approximately 10% for each minute of delay between occurrence of the arrest and the delivery of defibrillation therapy.

Trained lay caregivers are a new group of AED operators. For example, spouses of heart attack victims may become trained as lay caregivers. Lay caregivers rarely have opportunities to defibrillate or deliver CPR, and thus they can be easily intimidated by an AED during a medical emergency. Consequently, such lay providers may be reluctant to purchase or use AEDs when needed, or might tend to wait for an ambulance to arrive rather than use an available AED, out of concern that the lay provider might do something wrong.

Some trained medical providers, e.g., specialists such as obstetricians, dermatologists, and family care practitioners, also rarely have the opportunity to perform CPR and/or defibrillate, and thus may be uneasy about doing so. Concerns about competence are exacerbated if training is infrequent, leading the caregiver to worry that he or she may not be able to remember all of the recommended resuscitation protocol steps and/or their correct sequence.

Similarly, both medical and lay caregivers may be hesitant to provide CPR and rescue breathing, or may be unsure when these steps should be performed, particularly if their training is infrequent and they rarely have the opportunity to use it.

It is well known to those skilled in the art, and has been shown in a number of studies, that CPR is a complex task with both poor initial learning as well as poor skill retention, with trainees often losing 80% of their initial skills within 6-9 months. It has thus been the object of a variety of prior art to attempt to improve on this disadvantageous condition. Aids in the performance of chest compressions are described in U.S. Pat. Nos. 4,019,501, 4,077,400, 4,095,590, 5,496,257, 6,125, 299, and 6,306,107, 6,390,996. U.S. Pat. Nos. 4,588,383, 5,662,690 5,913,685, 4,863,385 describe CPR prompting systems. AEDs have always included voice prompts as well as graphical instructions on flip charts or placards since the earliest commercial versions in 1974 to provide both correct timing and sequence for the complex series of actions required of the rescuer (caregiver) as well as placement of the defibrillation electrodes. U.S. patent application Ser. No. 09/952,834 and U.S. Pat. Nos. 6,334,070 and 6,356,785 describe defibrillators with an increased level of prompting including visual prompts either in the form of graphical instructions presented on a CRT or on printed labels with backlighting or emissive indicia such as light emitting diodes. AEDs since the 1970s have used the impedance measured between the defibrillation electrodes to determine the state of the AED as well as appropriate messages to deliver to the rescuer (e.g. "Attach Electrodes" if the initial prompts on the unit have been delivered and the impedance remains greater than some specified threshold) or to determine if there is excessive patient motion (as in U.S. Pat. No. 4,610,254.) U.S. Pat. No. 5,700,281 describes a device which uses the impedance of the electrodes to determine the state of the AED for delivering messages such as "Attach Electrodes". Enhanced prompting disclosed in these patents provides some benefit to the rescuer in improved adherence to the complex protocol required of them to successfully revive a cardiac arrest patient, but the enhanced prompting is usually not sufficient in real world situations. U.S. Pat. Nos. 5,662,690 and 6,356, 785 (and the commercially available OnSite defibrillator) attempts to improve prompting by providing a rescuer-accessible "Help" key that initiates more detailed prompting in cases in which the rescuer or test subject is confused. But testing has shown that with the heightened level of anxiety that accompanies a real cardiac arrest, rescuers rarely remember to press such a Help key. Even notifying the rescuer at the beginning of the protocol to press the Help key does not help a the confused rescuer press the Help key. Furthermore, even if the Help key is pressed, it is necessary to have the rescuer work through a series of user interface interactions via a touchscreen, softkeys or other input means, for the help software to determine at which step the rescuer is in need of additional instructions. Putting the user through these interactions with the help software detracts from the rescuer's ability to provide aid to the patient, and thus delays delivery of therapy.

AEDs have also been solely focused on defibrillation, which, while it provides the best treatment for ventricular fibrillation and certain tachycardias, is of no therapeutic benefit for the 60% of the cardiac arrest patients presenting in pulseless electrical activity (PEA) or asystole. As AEDs are becoming more prevalent in the home, there are also a host of other health problems that occur such as first aid as well as incidents related to chronic conditions such as asthma, diabetes or cardiac-related conditions for which the AED is of no benefit.

SUMMARY

In a first aspect, the invention features a device for assisting a caregiver in delivering therapy to a patient, the device comprising a user interface configured to deliver prompts to a caregiver to assist the caregiver in delivering therapy to a patient; at least one sensor configured to detect the caregiver's progress in delivering the therapy, wherein the sensor is other than an electrode in an electrical contact with the body; a memory in which a plurality of different prompts are stored; a processor configured to determine which of the different prompts should be selected for delivery based on the progress detected by the sensor.

Preferred implementations of this aspect of the invention may incorporate one or more of the following: There may be a plurality of sensors configured to detect the caregiver's progress in delivering the therapy, wherein each of the plurality of sensor is other than an electrode connected to the body. The processor may be configured to vary the time at which prompts are delivered based on the progress detected by the sensor. One or more additional sensors may be configured to detect the caregiver's progress in delivering the therapy, wherein the one or more additional sensors comprise an electrode in electrical contact with the body. The at least one sensor may comprise a photoelectric sensor on the electrode for assisting in detection of whether the electrode has been applied to clothing. The therapy may comprise a series of steps in a protocol, and at least two sensors may be configured to detect whether at least two of the steps in the protocol have been successfully completed. The processor may select a series of more detailed prompts for delivery to a user when progress is slower than a predetermined pace. The processor may be configured to slow down the rate at which prompts are delivered when progress is slower than a predetermined pace. The processor may be configured to choose from among at least three rates at which prompts are delivered, and the choice is based at least in part on the progress detected by the sensor. The progress detected by the sensors may comprise whether a step in the protocol has been initiated and whether the step has been completed. The user interface may deliver at least some of the prompts as oral instructions to be heard by the caregiver. The user interface may deliver at least some of the prompts as visual instructions to be seen by the caregiver. The user interface may comprise an electronic display. The electronic display may provide a series of images. The user interface may comprise a series of printed pages. The device may further comprise one or more detectors configured to detect which page of the series of pages is being viewed by the caregiver. The detectors may comprise magnetic sensors that detect the presence of magnetic members supported by the pages. The processor may be configured to provide prompts with a first level of detail when progress is occurring at or faster than a predetermined rate, and with a second level of detail more specific than the first level of detail when progress is occurring at or slower than the predetermined rate. The sensor may be configured to detect whether the caregiver has made a predetermined error in delivering the therapy, and the processor may be configured to deliver one or more prompts designed to assist the user in correcting the predetermined error. The progress detected by the sensors may comprise whether a step in the protocol has been initiated and whether the step has been completed, and the processor may be configured to pause in delivery of prompts if a step has been initiated but not completed, and no predetermined error associated with the step has been detected. The device may be configured to assist a caregiver in delivering therapy for one or more cardiac malfunctions. The device may be configured to assist a caregiver in delivering therapy for one or more cardiac malfunctions. The device may be configured to assist a caregiver in delivering chest compressions. The device may be configured to assist a caregiver in delivering CPR. The device may be configured to assist a caregiver in delivering an electrical stimulus to the heart. The electrical stimulus may include defibrillation. The electrical stimulus may include pacing.

The device may comprise a defibrillator; and electrodes constructed to acquire data, indicative of the heart rhythm of the patient and indicative of whether the electrodes are properly placed on the patient and to deliver a defibrillating shock if appropriate. The device may further comprise on a portion of a housing for the device, a series of graphics configured to prompt a caregiver to perform a sequence of steps appropriate for treating a victim of suspected cardiac arrest The graphics may include a picture configured to prompt the caregiver to check the patient for responsiveness. The graphics may include a picture configured to prompt the caregiver to call for emergency assistance. The graphics may include a picture configured to prompt the caregiver to open the patient's airway. The graphics may include a picture configured to prompt the caregiver on how to open the patient's airway. The graphics may include a picture configured to prompt the caregiver to check the patient for signs of circulation. The graphics may include a picture configured to prompt the caregiver to attach the electrodes to the patient. The graphics may include a picture configured to prompt the caregiver on where the electrodes should be attached. The graphics may include a picture configured to prompt the caregiver to stand clear of the patient. The graphics may include a picture configured to prompt the caregiver to press a treatment button to cause the device to administer a defibrillating shock. The graphics may include a picture configured to prompt the caregiver to perform CPR. The graphics may include one or more pictures illustrating procedures for chest compressions and rescue breathing. The pictures may include a heart symbol indicating the location of the treatment button. The device may include a treatment button configured to be pressed by the caregiver to cause the defibrillator to administer a defibrillating shock. The device may further include a light source associated with each of the graphics in the series. The device may comprise electronics configured to sequentially illuminate the light sources. The graphics may include one or more pictures selected from the group consisting of: a picture configured to prompt the caregiver to check the patient for responsiveness; a picture configured to prompt the caregiver to call for emergency assistance; a picture configured to prompt the caregiver to open the patient's airway; a picture configured to prompt the caregiver to check the patient for signs of circulation; a picture configured to prompt the caregiver to attach the electrodes to the patient; a picture configured to prompt the caregiver to stand clear of the patient; and a picture configured to prompt the caregiver to perform CPR. The graphics may include a picture configured to prompt the caregiver to press a treatment button to cause the defibrillator to administer a defibrillating shock. The graphics may include one or more pictures selected from the group consisting of: a picture configured to prompt the caregiver to check the patient for responsiveness; a picture configured to prompt the caregiver to call for emergency assistance; a picture configured to prompt the caregiver to open the patient's airway; a picture configured to prompt the caregiver to check the patient for signs of circulation; a picture configured to prompt the caregiver to attach the electrodes to the patient; a picture configured to prompt the caregiver to stand clear of the patient; and a picture configured to prompt the caregiver to perform CPR. The light sources may comprise LEDs. The audio prompts may be associated with the series of graphics and are given sequentially to guide the caregiver through the sequence of steps. The device may further comprise electronics configured to sequentially illuminate the light sources, wherein the audio prompts are associated with the series of graphics and with the sequential illumination of the light sources, to guide the caregiver through the sequence of steps. The device may further comprise electronics configured to measure the time elapsed from the time at which the caregiver turned the power on to activate the defibrillator, and at least some of the audio prompts are timed to occur based on the elapsed time. At least some of the graphics may be provided on a cover portion of the defibrillator device housing. At least some of the graphics may be provided on the outside of the cover portion of the device. The graphics on the cover portion may include a picture indicating that the cover should be removed from the device. The cover portion may include a space provided for local emergency information. The cover portion may include a window behind which a card bearing local emergency information can be placed. At least some of the graphics may be provided in the form of backlit, translucent images. At least some of the graphics may be provided in the form of a decal. The device may further comprise buttons, associated with at least some of the graphics, which, when pressed, cause more detailed audio prompts related to the associated graphic to be output by the device. The graphics may include one or more pictures indicating that the caregiver should place a passive airway support under the shoulders of the patient. The graphics may include a picture configured to prompt the caregiver to check to see if the patient is breathing. The prompts and graphical interface may illustrate the entire sequence of resuscitation activities that are recommended by the American Heart Association. The prompts may include instructions for performing first aid. The device may comprise a cover to the device whose removal the processor is capable of detecting; and a series of bound pages on the face of the device under the cover with one or more sensors for determining to which page the bound pages have been turned. The device may further comprise a portion of the device used specifically for storage of items commonly used in the course of providing aid such as bandaids, bandages, splints, antiseptic. The storage area may be partitioned into individual wells in which each of the items is stored and a detections means may be provided for determining which, if any, of the items has been removed by the user. Photoelectric sensors may be provided in each of the wells. The prompts and graphical interface may illustrate the Red Cross First Aid treatment protocols.

The device may include a cover whose removal the processor is capable of detecting; a defibrillator for delivering defibrillation shocks; electrodes configured to be attached to a patient, to acquire data indicative of the patient's heart rhythm and to deliver a defibrillating shock if appropriate; a storage area for said electrodes; and at least one sensor for determining if the electrodes have been removed from the storage area by the user. The storage area may be a compartment that is part of the housing of the device. The storage area may be a package removable from the housing of the device. The cover may be shaped for use as a neck rest for maintaining the patient's airway in the necessary open condition during CPR. A detection means may be provided for determining if the patient's head is correctly located on the cover while it is being used as a neck rest. The detection means may be provided by a pressure sensor. The detection means may be provided by a photoelectric sensor.

The device may further comprise a decision making system provided by a distributed network may comprise a remotely located human expert, an electronic processor in the device, and an electronic communication link between the human and electronic processor. The information transmitted over the communication link may be both voice and digital data.

The data may be bi-directional. The digital data may contain information about the device's location and the status of the device. The device may be capable of being remotely controlled by the human expert. The electronic processor may revert to providing internally generated responsive feedback prompts if the communication link is lost to the remotely located human expert. The device may further comprise a decision-making system comprising circuitry and an electronic processor located in the device. The device may further comprise a decision making system provided by a distributed network comprising a remotely located electronic processing system, a local electronic processing system in the device and an electronic communication link between the remote and local electronic processing system. The device may further comprise a processing system that measures and records the times required for a user to complete a sequence of steps and/or sub-steps in a protocol, and, based on the measured times adjusting the rate of the prompting delivered by the processor and user interface. The adjusting may be based on a comparison of the measured times with a set of stored values. The device may comprise decision-making circuitry for evaluating the difference between the measured times and the set of stored values. The device may further comprise elements for correctly identifying a set of voice commands delivered by the user and performing a set of actions in response to those user voice commands.

In a second aspect, the invention features an automatic external defibrillator for assisting a caregiver in delivering resuscitation therapy to a patient, the defibrillator comprising a memory in which a plurality of different prompts are stored; a processor configured to determine which of the different prompts should be selected for delivery; a user interface configured to deliver the selected prompts to a caregiver to assist the caregiver in delivering therapy to a patient, wherein the user interface comprises a series of printed pages and one or more detectors configured to detect which page of the series of pages is being viewed by the caregiver.

Preferred implementations of this aspect of the invention may incorporate one or more of the following. Detectors may comprise magnetic sensors that detect the presence of magnetic members supported by the pages.

Among the many advantages of the invention (some of which may be achieved only in some of its various aspects and implementations) are that the invention provides a more comprehensive and effective system for prompting users in the delivery of care for first aid, chronic health problems as well as cardiac arrest.

The invention can provide the further benefit that a device can intelligently vary the amount of detail to provide in prompts to the caregiver. In currently available devices, the prompting has been optimized for the average user, and this is both frustrating and obstructive for the expert user; the more detailed prompting is not needed by the expert user and actually delays delivery of treatment. The invention can eliminate the need for this compromise, by intelligently delivering prompts needed by the particular user.

Other features and advantages of the invention will be apparent from the description and drawings, and from the claims.

DESCRIPTION OF DRAWINGS

FIG. 1 is a perspective view of an AED with its cover on.
FIGS. 7a and 7b list the audio prompts used in the flowcharts shown in FIGS. 6a-6e.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

The terms "caregiver", "rescuer" and "user" are used interchangeably and refer to the operator of the device providing care to the patient.

Figure 1:
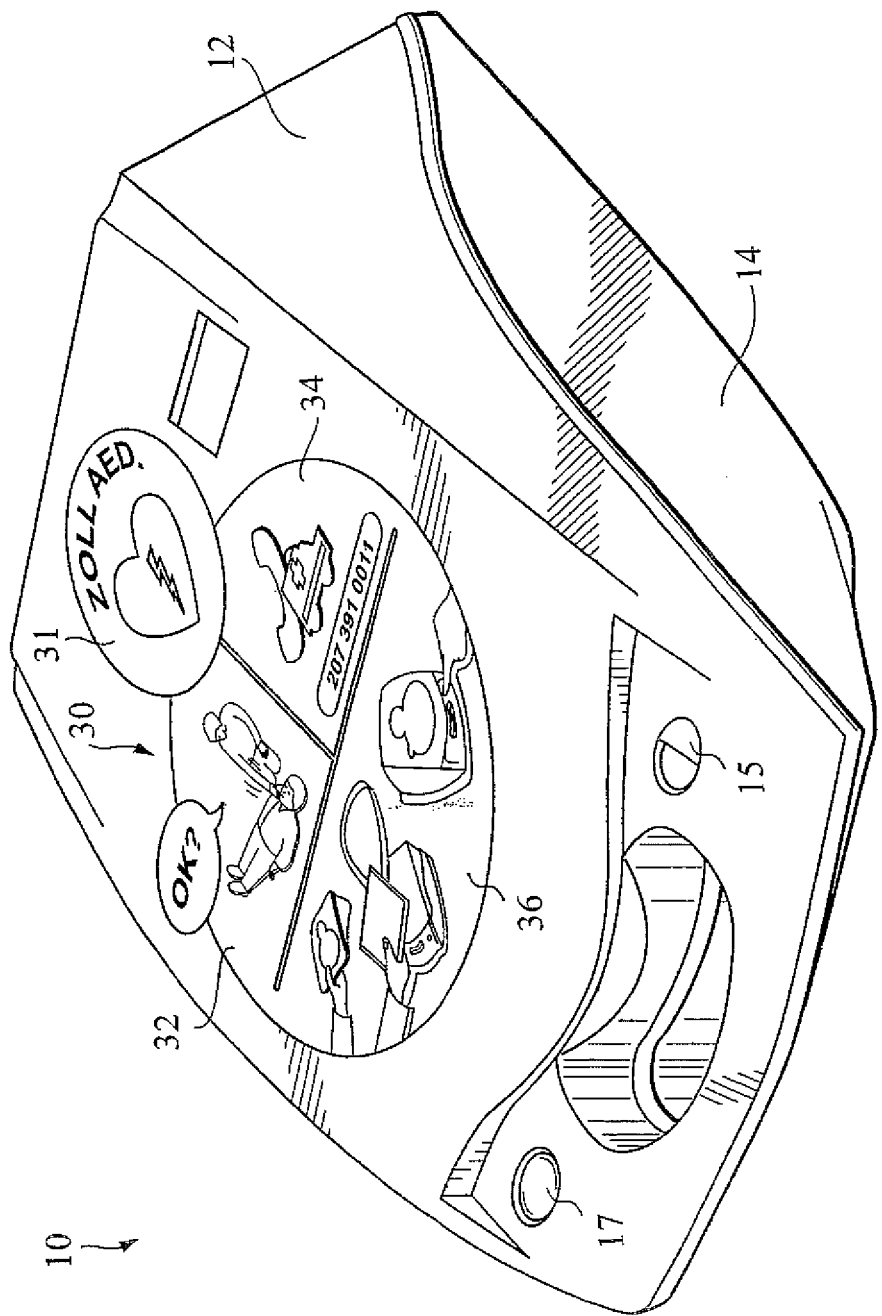
Figure 2:
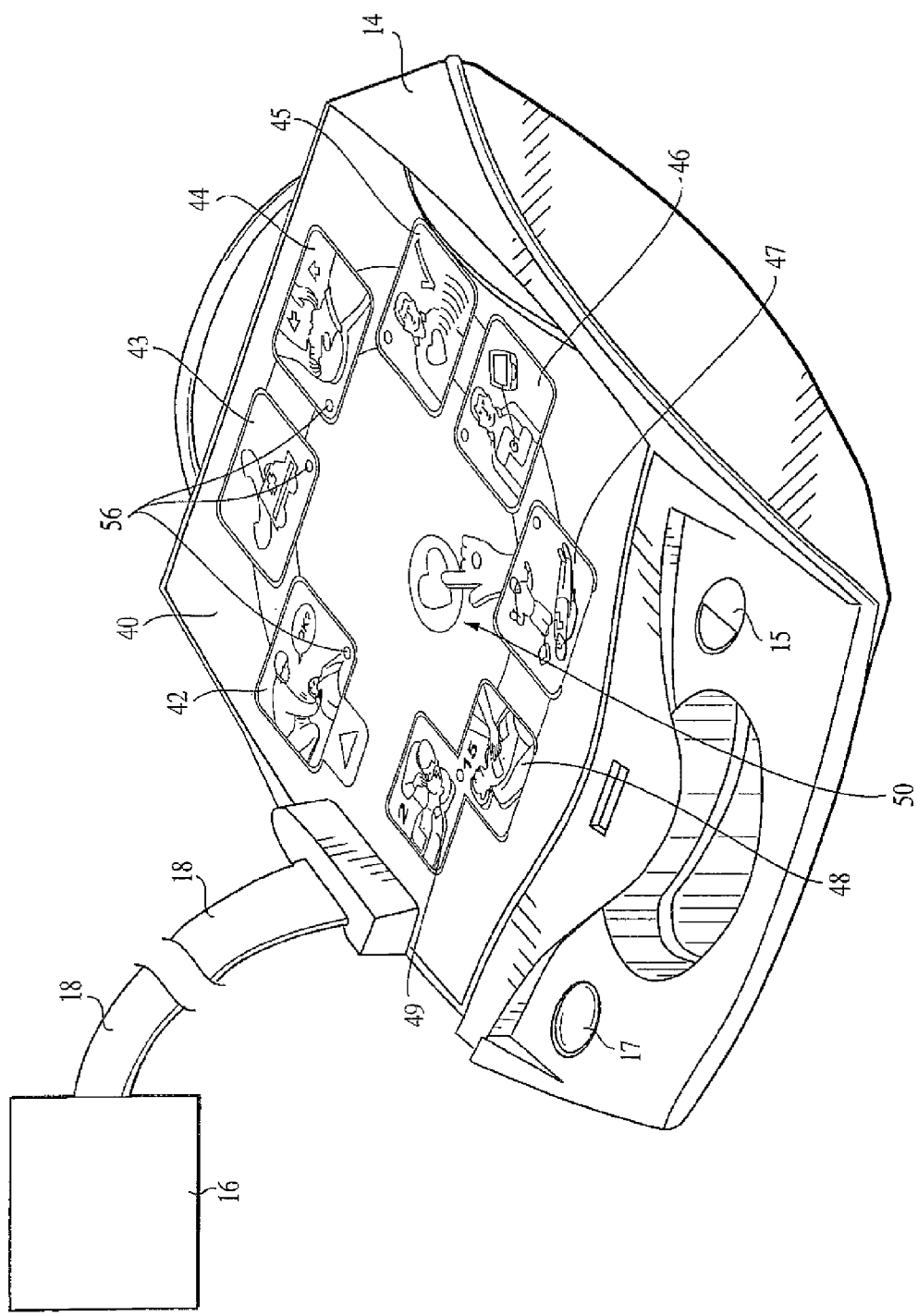
FIG. 2 is a perspective view of the AED of FIG. 1 with the cover removed.

Referring to FIGS. 1 and 2, an automated external defibrillator (AED) 10 includes a removable cover 12 and a device housing 14. The defibrillator 10 is shown with cover 12 removed in FIG. 2. An electrode assembly 16 (or a pair of separate electrodes) is connected to the device housing 14 by a cable 18. Electrode assembly 16 is stored under cover 12 when the defibrillator is not in use.

Figure 3:
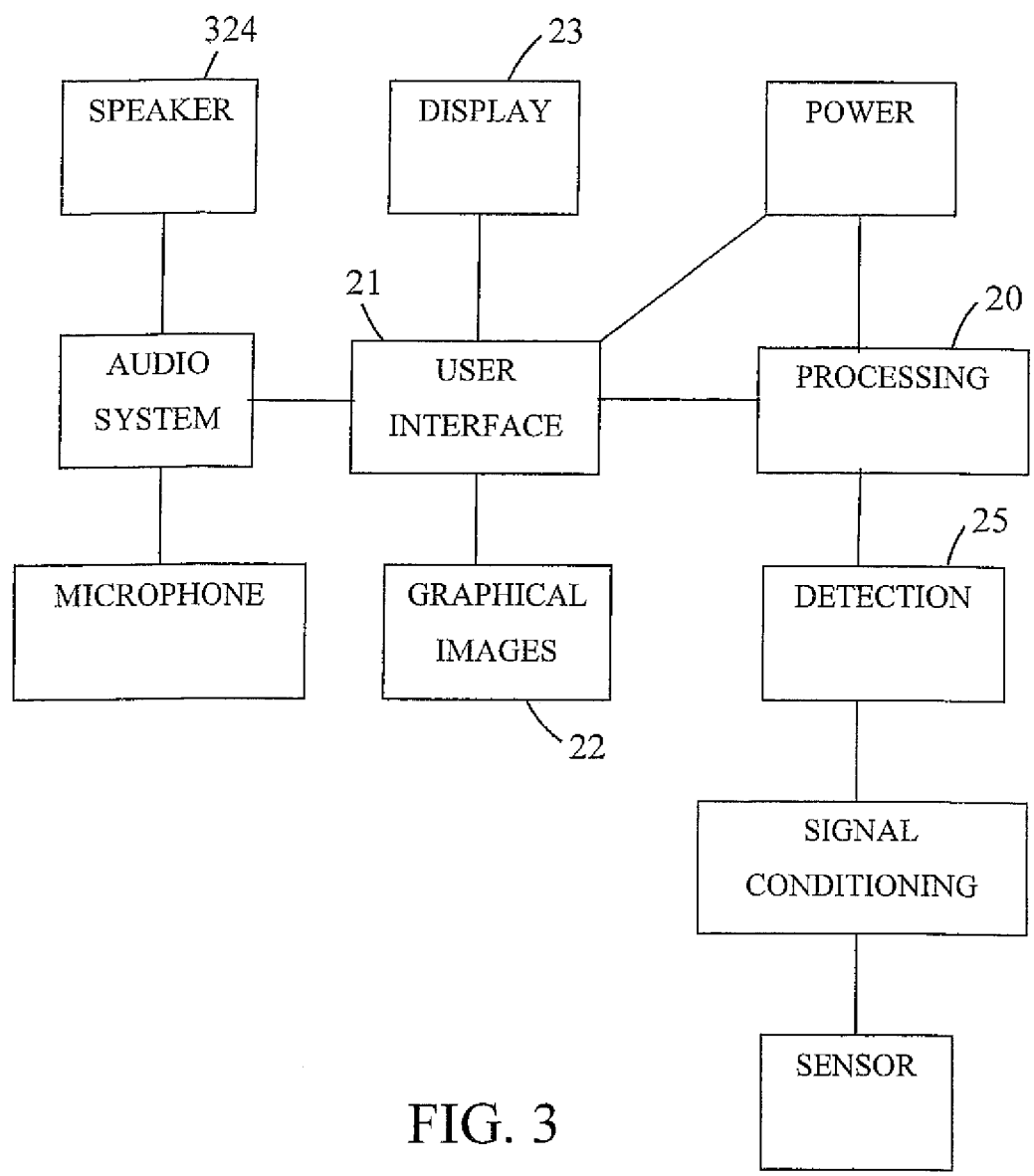
FIG. 3 is a block diagram of the AED.
Figure 4:
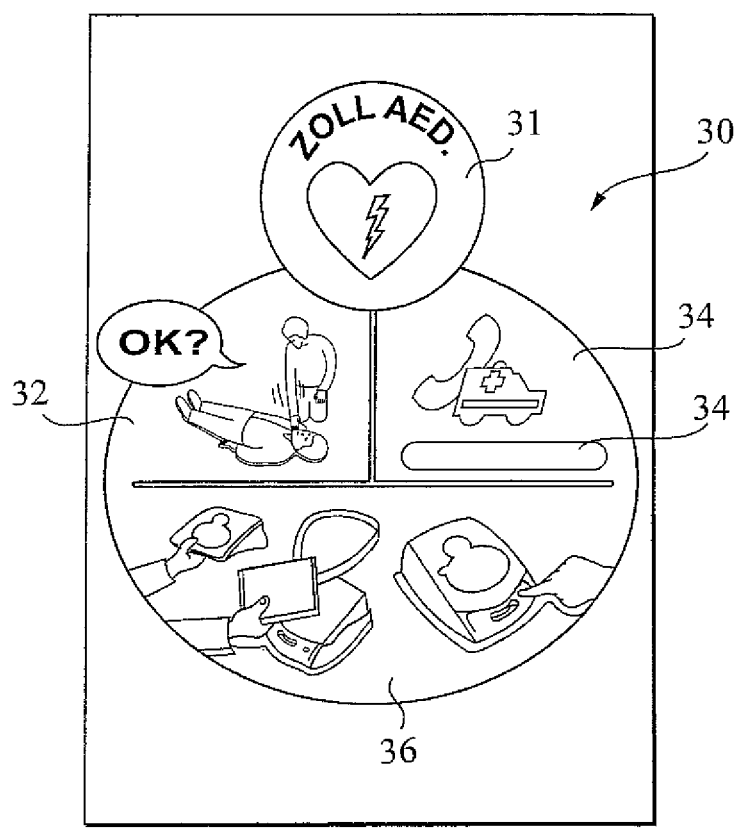
FIG. 4 is a plan view of the graphical interface decal used on the cover of the AED of FIG. 1.

Referring to FIG. 3, the AED includes circuitry and software 20 for processing, a user interface 21 including such elements as a graphical 22 or text display 23 or an audio output such as a speaker 24, and circuitry and/or software 25 for detecting a caregiver's progress in delivering therapy—e.g., detecting whether one or more of a series of steps in a protocol has been completed successfully In some preferred implementations, the detecting also includes the ability to determine both whether a particular step has been initiated by a user and additionally whether that particular step has been successfully completed by a user. Based on usability studies in either simulated or actual use, common user errors are determined and specific detection means are provided for determining if the most prevalent errors have occurred.

If it is determined that the current step in the protocol has not been completed, then the processor will pause the currently-scheduled sequence of instructions. If, for instance, it has been determined that a particular step has been initiated but not completed, but none of the common errors has occurred subsequent to initiation of the particular step, then the processor may simply provide a pause while waiting for the user to complete the step. If, after waiting for a predetermined period of time based on prior usability tests, there has been no detection of the step completion, the processor may initiate a more detailed set of prompts, typically at a slower sequence rate, describing the individual sub-steps that comprise a particular step. If one of the common errors is detected while waiting for completion of the step, the processor may initiate a sequence of instructions to correct the user's faulty performance.

Device housing 14 includes a power button 15 and a status indicator 17. Status indicator 17 indicates to the caregiver whether the defibrillator is ready to use.

The cover 12 includes a cover decal 30 (FIG. 1) including a logo 31 and a series of graphics 32, 34 and 36. Logo 31 may provide information concerning the manufacturer of the device and that the device is a defibrillator (e.g., "ZOLL AED", as shown in FIG. 1, indicating that the device is a Semi-Automatic External Defibrillator available from Zoll Medical). Graphics 32, 34 and 36 lead the caregiver through the initial stages of a cardiac resuscitation sequence as outlined in the AHA's AED treatment algorithm for Emergency Cardiac Care pending arrival of emergency medical personnel. (See "Guidelines 2000 for Cardiopulmonary Resuscitation and Emergency Cardiovascular Care. Supplement to Circulation," Volume 102, Number 8, Aug. 22, 2000, pp. I-67.) Thus, graphic 32, showing the caregiver and patient, indicates that the caregiver should first check the patient for responsiveness, e.g., by shaking the patient gently and asking if the patient is okay. Next, graphic 34, showing a telephone and an emergency vehicle, indicates that the caregiver should call for emergency assistance prior to administering resuscitation. Finally, graphic 36 indicates that after these steps have been performed the caregiver should remove the cover 12 of the defibrillator, remove the electrode assembly 16 stored under the lid, and turn the power on by depressing button 15. The graphics are arranged in clockwise order, with the first step in the upper left, since this is the order most caregivers would intuitively follow. However, in this case the order in which the caregiver performs the steps is not critical, and thus for simplicity no other indication of the order of steps is provided.

The device housing includes a device housing decal 40, shown in FIG. 2. The graphics are configured to lead the caregiver through the entire resuscitation sequence, as will be explained below with reference to FIGS. 6a-6e. Decal 40 also includes a center graphic 50, which includes representations of a hand and a heart. Center graphic 50 overlies a treatment button which, when depressed, causes the defibrillator to deliver a defibrillating shock to the electrode assembly 16.

Each of the graphics on device housing decal 40 is accompanied by a light source that can be temporarily illuminated to indicate that the illuminated step should be performed at that particular time. These light sources guide the caregiver, step-by-step, through the resuscitation sequence, indicating which graphic should be viewed at each point in time during resuscitation.

The light source for each of the graphics 42-50 is preferably an adjacent LED (LEDs 56, FIG. 2). The heart 54 may be translucent and backlit by a light source in the device housing (not shown). Alternatively, the heart may include an adjacent LED (not shown) and/or the hand 52 may include an LED 57 as shown. Programmable electronics within the device housing 14 are used to determine when each of the light sources should be illuminated.

In some preferred implementations, a liquid crystal display 51 is used to provide the more detailed graphical prompts when a user is unable to complete the rescue sequence on their own. In these implementations, the purpose of the printed graphics is to provide a more general indication of the current step in the overall sequence, e.g. airway graphics 44 provides an indication that the rescuer should be performing the "Open Airway. Check for Breathing." sub-sequence, but may not provide a detailed enough description for someone who has forgotten the correct actions to perform. In an alternative embodiment, the graphical instructions may be provided by a larger version of the liquid crystal display (LCD) 51 whereby the LED-lit printed instructions are eliminated or removed and most or all of the graphical instructions are provided by the LCD 30. In this case, the LCD 51 will automatically show the more detailed instructions when it determines that the user is unable to properly perform the action.

The programmable electronics may also provide audio prompts, timed to coincide with the illumination of the light sources and display of images on the liquid crystal display 51, as will also be discussed below with reference to FIGS. 6a and 6e.

Figure 10A:
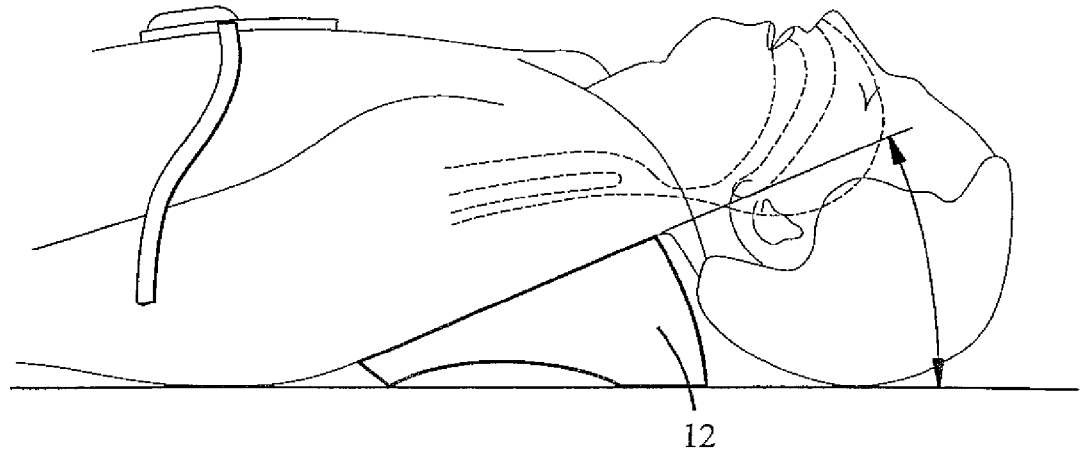
FIGS. 10a and 10b are side views of a patient with and without the cover placed beneath the shoulders, to show the effect on the patient's airway of placing the cover beneath the shoulders.
Figure 10B:
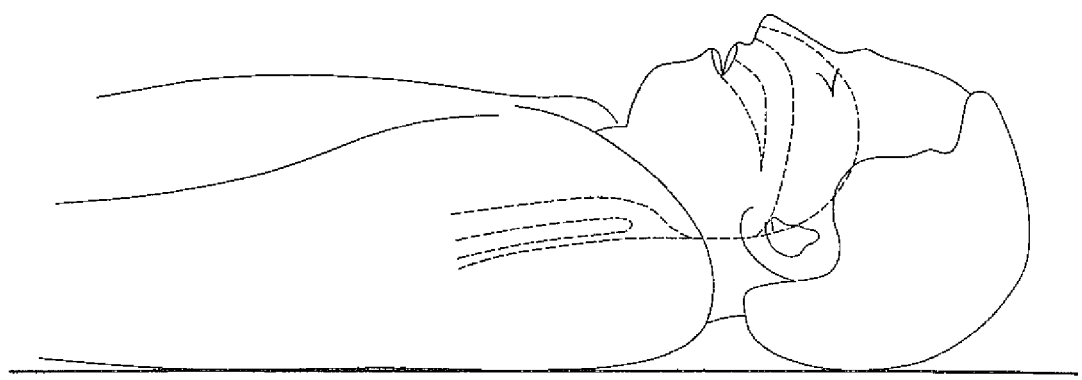

The cover 12 is constructed to be positioned under a patient's neck and shoulders, as shown in FIGS. 10a and 10b, to support the patient's shoulders and neck in a way that helps to maintain his airway in an open position, i.e., maintaining the patient in the head tuck-chin lift position. The cover is preferably formed of a relatively rigid plastic with sufficient wall thickness to provide firm support during resuscitation. Suitable plastics include, for example, ABS, polypropylene, and ABS/polypropylene blends.

Prior to administering treatment for cardiac arrest, the caregiver should make sure that the patient's airway is clear and unobstructed, to assure passage of air into the lungs. To prevent obstruction of the airway by the patient's tongue and epiglottis (e.g., as shown in FIG. 10a), it is desirable that the patient be put in a position in which the neck is supported in an elevated position with the head tilted back and down. Positioning the patient in this manner is referred to in the American Heart Association Guidelines for Cardiopulmonary Resuscitation and Emergency Cardiovascular Care as the "head tilt-chin lift maneuver." The head tilt-chin lift position provides a relatively straight, open airway to the lungs through the mouth and trachea. However, it may be difficult to maintain the patient in this position during emergency treatment.

The cover 12 has an upper surface 24 that is inclined at an angle A (FIG. 9a) of from about 10 to 25 degrees, e.g., 15 to 20 degrees, so as to lift the patient's shoulders and thereby cause the patient's head to tilt back. The upper surface 24 is smoothly curved to facilitate positioning of the patient. A curved surface, e.g., having a radius of curvature of from about 20 to 30 inches, generally provides better positioning than a flat surface. At its highest point, the cover 12 has a height H (FIG. 9) of from about 7.5 to 10 cm. To accommodate the width of most patients' shoulders, the cover 12 preferably has a width of at least 6 inches, e.g., from about 6 to 10 inches. If the cover 12 is not wide enough, the patient's neck and shoulders may move around during chest compressions, reducing the effectiveness of the device. The edge of the cover may also include a lip 11 (FIG. 9) or gasket (not shown) to prevent water from entering the housing when the cover is in place. The positions shown in FIGS. 10a and 10b (a patient in the head lift-chin tilt position and a patient with a closed airway) are also shown in the AHA Guidelines for Cardiopulmonary Resuscitation and Emergency Cardiovascular Care, Aug. 22, 2000, p. I-32, FIGS. 7 and 8.

Figure 8:
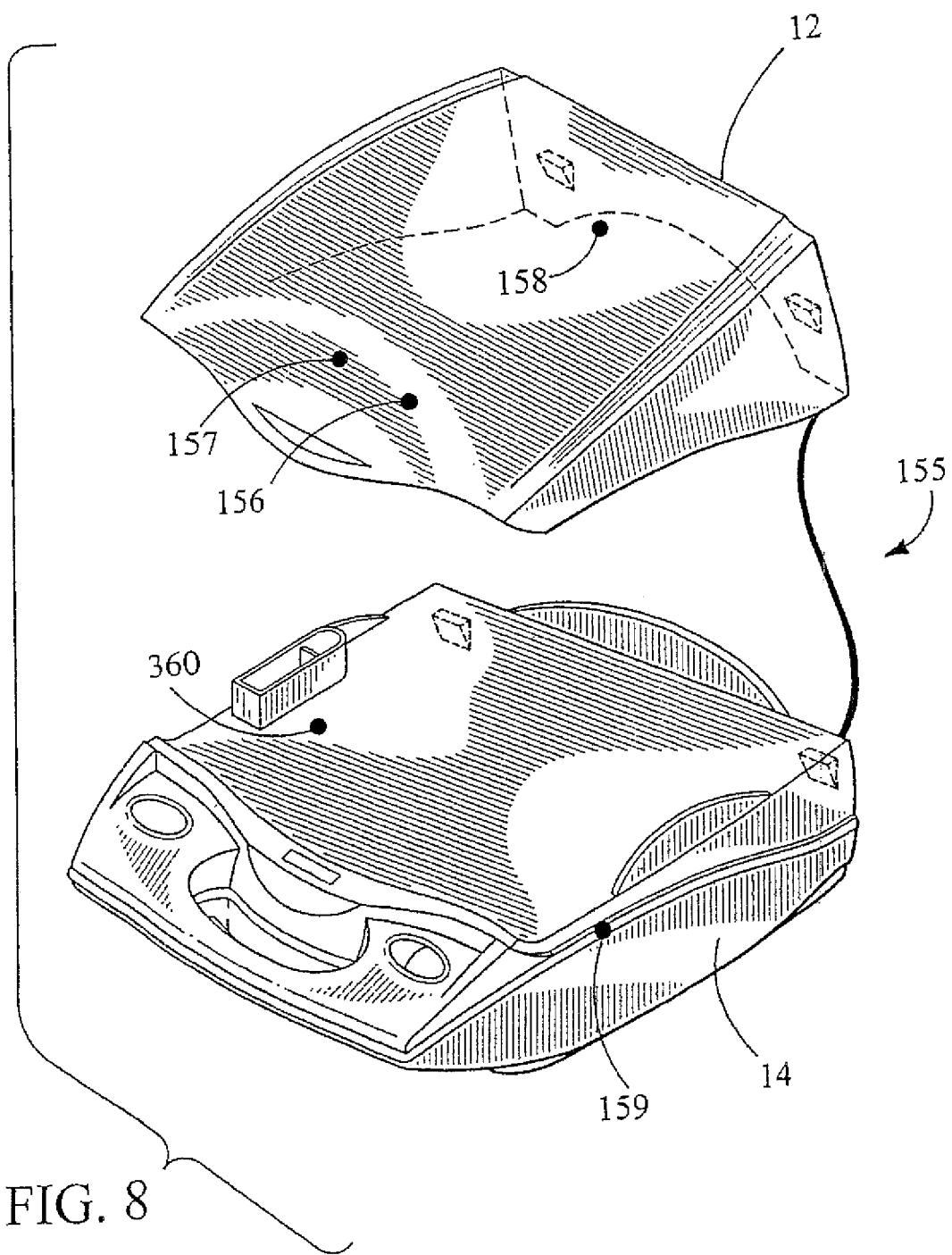
FIG. 8 is an exploded perspective view of the cover and housing.
Figure 9:
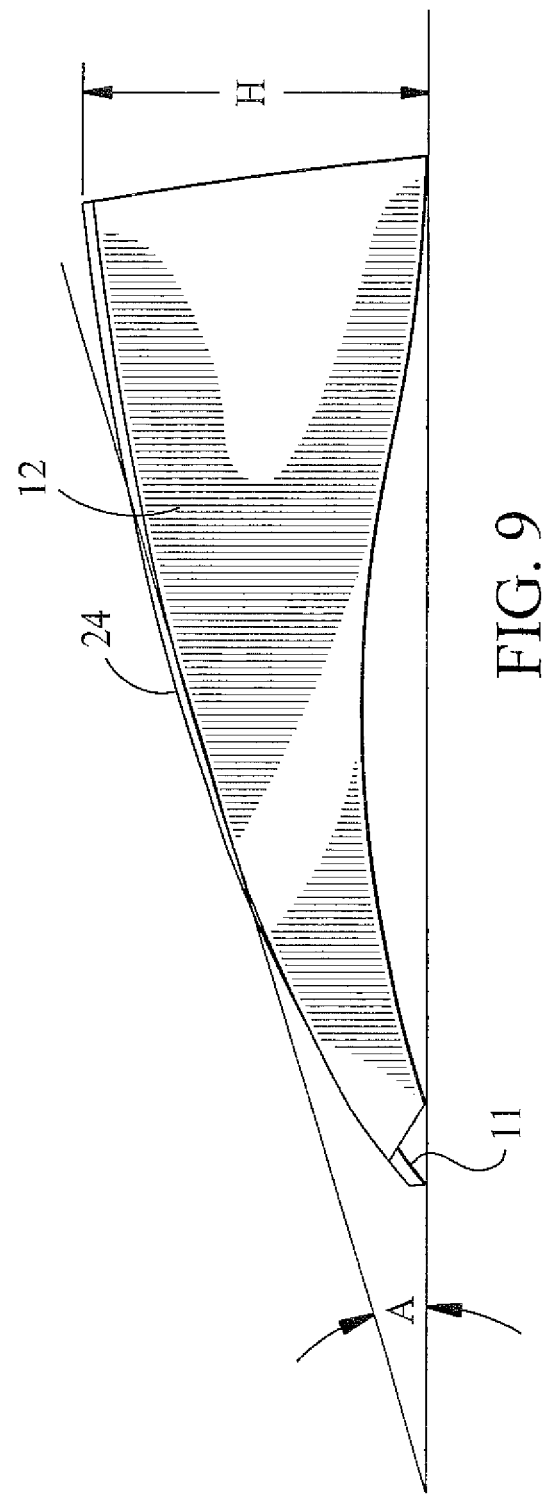
FIG. 9 is a side plan view of the cover indicating angle 'A'.

The cover 12 is provided with one or more sensors for determining if the patient's shoulders have been properly positioned on the cover 12. Referring to FIG. 8, two photo-electric sensors 156, 157 are used to determine if the cover has been placed underneath the patient's back. The sensors 156, 157 are located along the acute edge of the cover 12, with one facing inward and one facing outward with the cable 155 providing both power to the sensors 156, 157 as well as detection of the sensor output. If the cover 12 is upside down, the inner sensor 156 will measure a higher light level than the outer sensor 157; if the cover has been placed with the acute edge facing toward the top of the patient's head, then the outer sensor 157 will measure higher than the inner sensor 156 and will also exceed a pre-specified level. In the case of a properly positioned cover, both inner 156 and outer sensor 157 outputs will be below a pre-specified level. In another embodiment, the detections means is provided by a pressure sensor 158 located underneath the cover decal. Referring to FIG. 6*c*, if the processing means 20 detects that the cover is upside down, it will cause an audible prompt to be delivered to the user that is more detailed than the original prompt. The processing means 20 will also slow down the rate of speech of the audio prompts. If the cover is still upside down after a predetermined period of time, the processing means 20 will deliver an even more detailed message on how to properly place the cover. If, after three attempts to get the user to properly position the cover 12, the processing means 20 will deliver the next audio prompt without further waiting for proper placement of the cover 12.

In the preferred embodiment, the defibrillator includes communication capability such as cell phone, global positioning system (GPS) or simpler wireless phone capability. Preferably, both cell phone and GPS are included in the device. The cell phone is preconfigured to automatically dial the Emergency Response Center (ERC) in the community in which it is located such as "911" in much of the United States. The cell phone service is chosen which is able to provide voice, data, as well as GPS capability. Thus in response to a command by the device to "Call 911 by Pressing the Phone button", the device automatically dials 911 and the built-in speaker 360 and microphone 159 on the device function to provide speakerphone capability. If a connection is successfully made to the emergency response center, the device transmits its exact location based on its GPS capability and also can transmit to the response center the status of the defibrillator. In more advanced modes, the emergency response center can remotely control the operation of the defibrillator via the bi-directional data capability. When a connection is made to the ERC and emergency response personnel (ERP), the automatic voice prompting of the defibrillator can be remotely de-activated by the ERP so as not to distract the rescuer from the instructions given by the ERP. While coaching the rescuer via the speakerphone capability in the defibrillator, the ERP can utilize the responsive feedback prompting functionality of the device to provide more accurate coaching of the rescuer. It is well known, however, that cell phone and other wireless communication methods are not especially reliable even under the best circumstances, and are often completely unavailable in industrial facilities, basements, etc., thus it is important to provide a means of automatically reverting to the mode wherein the device provides all responsive feedback prompts to the user when the processor detects that the communication link has been lost. Additional prompts will also be provided to the user to assuage any concern they might have that the connection to the human expert has been lost (e.g. "Communication has been temporarily lost to 911 personnel. Don't worry. This AED is able to perform all steps and help you through this procedure."). When a communication link has been lost, the device will preferably automatically begin recording all device and patient status as well as all audio received by the built-in microphone. If the communication link is subsequently reacquired, the device will preferably automatically transmit the complete event, including patient, device and audio data, acquired during the time communication was not available, providing ERP valuable data to help in their medical decision-making. The ERP may remotely control the defibrillator via a bi-directional communication link that transmits both voice and data.

In another embodiment, a remote computer located at the ERC, that is more capable than the processor in the device may provide the remote decision-making capability. The remote computer would run artificial intelligence software utilizing such techniques, e.g., as fuzzy logic, neural nets and intelligent agents to provide prompting to the user.

Figure 6A:
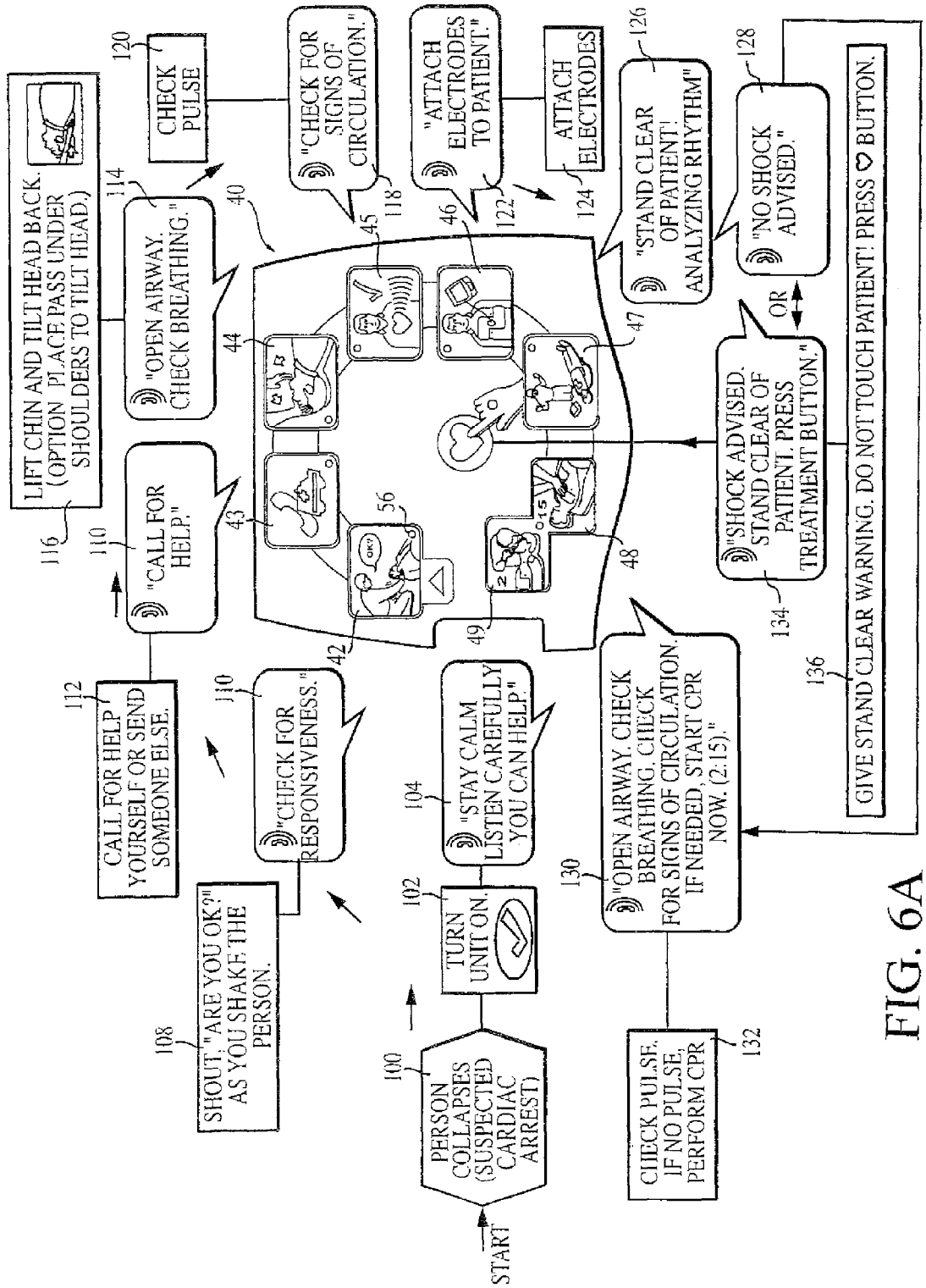
FIG. 6a-6e are flow charts indicating audio prompts provided during use of the AED of FIG. 1 and steps to be performed by the caregiver in response to the graphical and audio prompts.
Figure 6B:
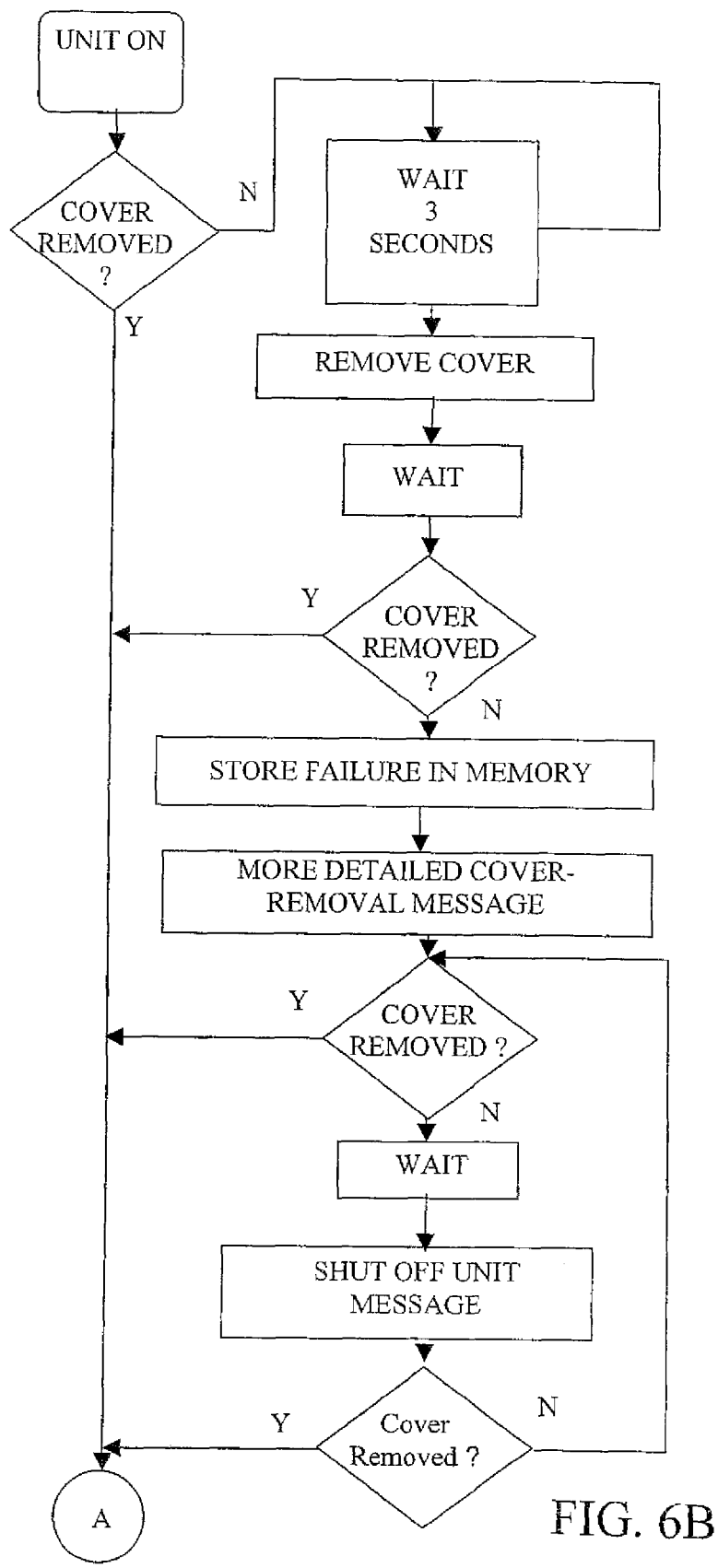
Figure 6C:
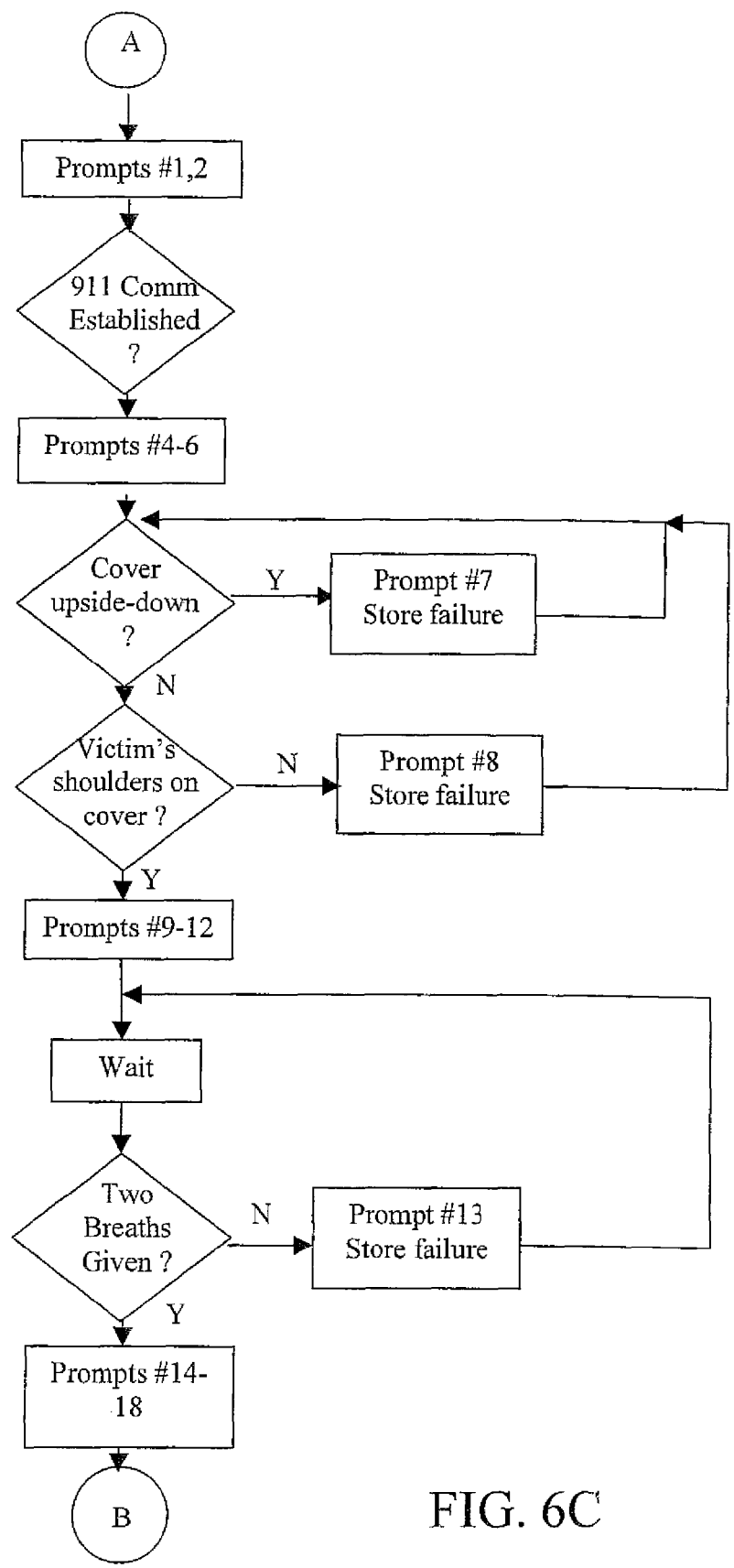
Figure 6D:
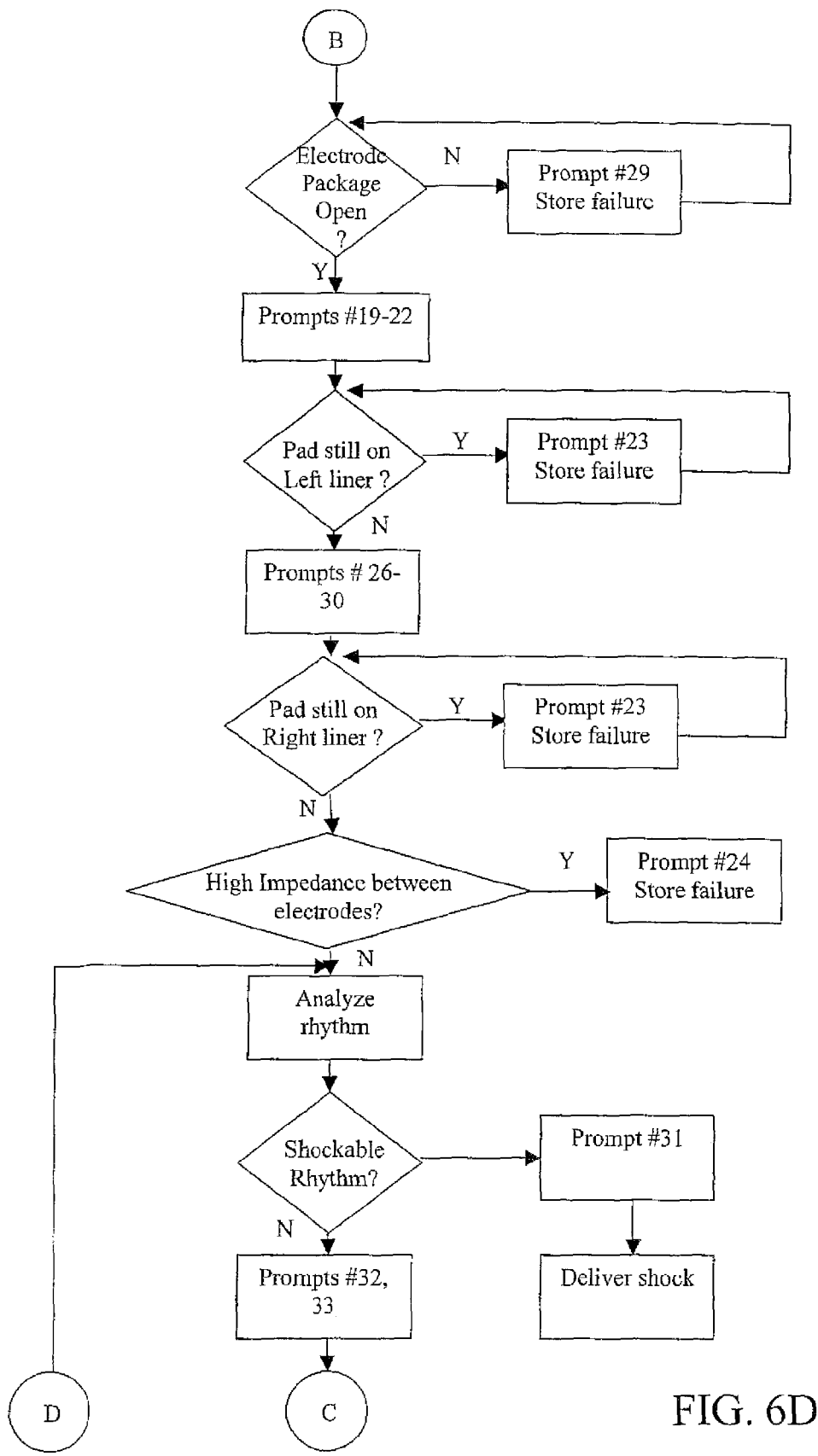
Figure 6E:
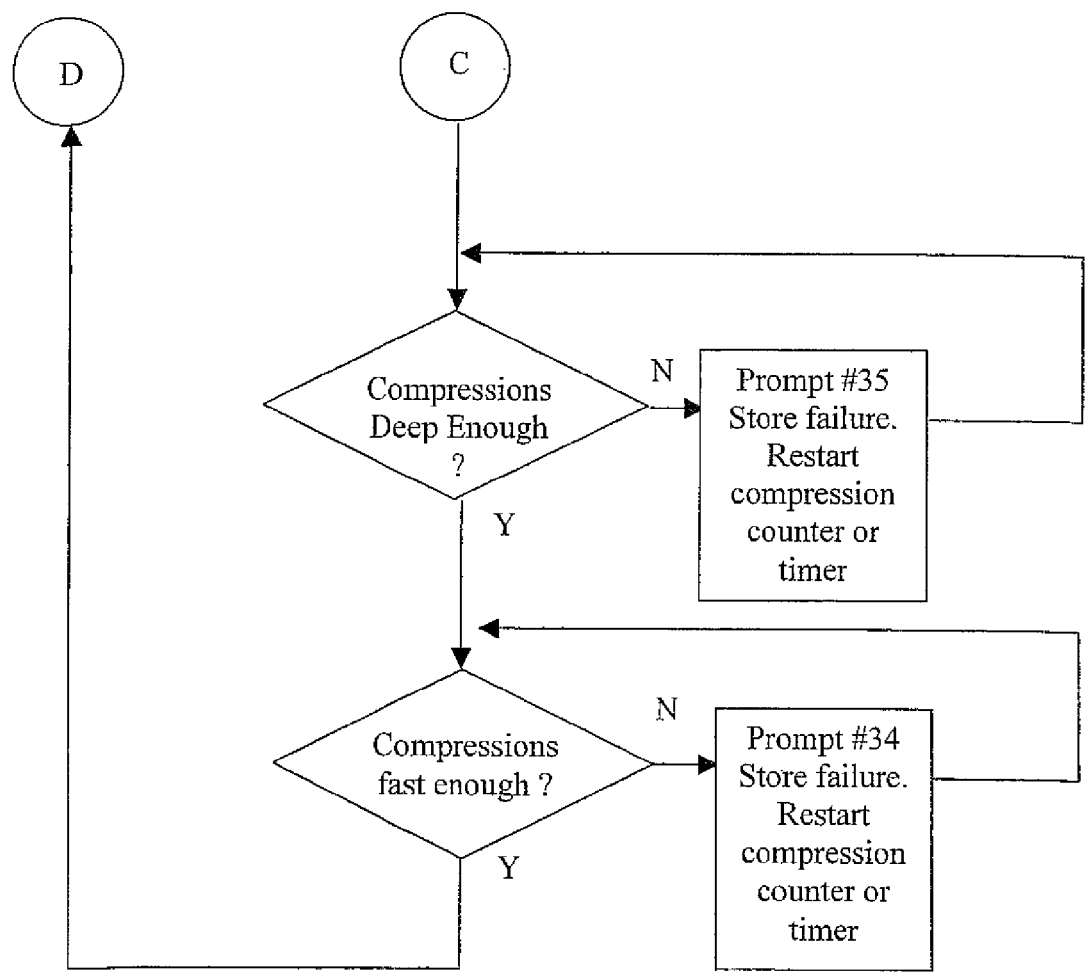

FIG. 6*a* illustrates, in flow chart form, the default graphical and audio prompts provided by the device for a caregiver performing resuscitation. The prompts shown in the figure do not include responsive feedback prompts by the device that provide more detailed instructions depending on whether particular sequences have been successfully completed by the caregiver. The text in boxes indicates steps performed by the caregiver. The text in caption balloons, with ear symbols, indicates audio prompts generated by the defibrillator. FIGS. 6*b*-6*e* provide flowcharts of more detailed responsive feedback prompts (the content of which are shown in FIGS. 7*a*, 7*b*) that may be provided to supplement the steps of calling for help, open airway/check for breathing, and defibrillation electrode application.

Thus, when a person collapses and a caregiver suspects that the person is in cardiac arrest 100 (FIG. 6*a*), the caregiver first gets the defibrillator and turns the power on 102. If the unit passes its internal self tests, and is ready for use, this will be indicated by indicator 17, as discussed above. Next, the defibrillator prompts the caregiver with an introductory audio message, e.g., "Stay calm. Listen carefully" (audio prompt 104).

Shortly thereafter, the defibrillator will prompt the caregiver with an audio message indicating that the caregiver should check the patient for responsiveness (audio prompt 106). Simultaneously, the LED adjacent graphic 42 will light up, directing the caregiver to look at this graphic. Graphic 42 will indicate to the caregiver that she should shout "are you OK?" and shake the person (step 108) in order to determine whether the patient is unconscious or not.

After a suitable period of time has elapsed (e.g., 2 seconds), if the caregiver has not turned the defibrillator power off (as would occur if the patient were responsive), the defibrillator will give an audio prompt indicating that the caregiver should call for help (audio prompt 110). Simultaneously, the LED adjacent graphic 42 will turn off and the LED adjacent graphic 43 will light up, directing the caregiver's attention to graphic 43. Graphic 43 will remind the caregiver to call emergency personnel (step 112), if the caregiver has not already done so.

After a suitable interval has been allowed for the caregiver to perform step 112 (e.g., 2 seconds since audio prompt 110) the defibrillator will give an audio prompt indicating that the caregiver should open the patient's airway and check whether the patient is breathing (audio prompt 114). The LED adjacent graphic 43 will turn off, and the LED adjacent graphic 44 will light up, directing the caregiver's attention to graphic 44, which shows the proper procedure for opening a patient's airway. This will lead the caregiver to lift the patient's chin and tilt the patient's head back (step 116). The caregiver may also position an airway support device under the patient's neck and shoulders, if desired, as discussed below with reference to FIGS. 10a, 10b. The caregiver will then check to determine whether the patient is breathing.

After a suitable interval (e.g., 15 seconds since audio prompt 114), the defibrillator will give an audio prompt indicating that the caregiver should check for signs of circulation (audio prompt 118), the LED adjacent graphic 44 will turn off, and the LED adjacent graphic 45 will light up. Graphic 45 will indicate to the caregiver that the patient should be checked for a pulse or other signs of circulation as recommended by the AHA for lay rescuers (step 120).

After a suitable interval (e.g., 5 to 7 seconds since audio prompt 118), the defibrillator will give an audio prompt indicating that the caregiver should attach electrode assembly 16 to the patient (audio prompt 122), the LED adjacent graphic 45 will turn off, and the LED adjacent graphic 46 will light up. Graphic 46 will indicate to the caregiver how the electrode assembly 16 should be positioned on the patient's chest (step 124).

At this point, the LED adjacent graphic 47 will light up, and the defibrillator will give an audio prompt indicating that the patient's heart rhythm is being analyzed by the defibrillator and the caregiver should stand clear (audio prompt 126). While this LED is lit, the defibrillator will acquire ECG data from the electrode assembly, and analyze the data to determine whether the patient's heart rhythm is shockable. This analysis is conventionally performed by AEDs.

If the defibrillator determines that the patient's heart rhythm is not shockable, the defibrillator will give an audio prompt such as "No shock advised" (audio prompt 128). The LEDs next to graphics 48 and 49 will then light up, and the defibrillator will give an audio prompt indicating that the caregiver should again open the patient's airway, check for breathing and a pulse, and, if no pulse is detected by the caregiver, then commence giving CPR (audio prompt 130, step 132). Graphics 48 and 49 will remind the caregiver of the appropriate steps to perform when giving CPR.

Alternatively, if the defibrillator determines that the patient's heart rhythm is shockable, the defibrillator will give an audio prompt such as "Shock advised. Stand clear of patient. Press treatment button" (audio prompt 134). At the same time, the heart and/or hand will light up, indicating to the caregiver the location of the treatment button. At this point, the caregiver will stand clear (and warn others, if present, to stand clear) and will press the heart, depressing the treatment button and administering a defibrillating shock (or a series of shocks, as determined by the defibrillator electronics) to the patient (step 136).

After step 136 has been performed, the defibrillator will automatically reanalyze the patient's heart rhythm, during which audio prompt 126 will again be given and graphic 47 will again be illuminated. The analyze and shock sequence described above will be repeated up to three times if a shockable rhythm is repeatedly detected or until the defibrillator is turned off or the electrodes are removed. After the third shock has been delivered, the device will illuminate LEDs 48 and 49 and issue the audio prompts 130/132. The device will keep LEDs 48 and 49 illuminated for a period of approximately one minute indicating that if CPR is performed, it should be continued for the entire minute. "Continue CPR" audio prompts may be repeated every 15-20 seconds during this period to instruct the user to continue performing chest compressions and rescue breathing.

After approximately one minute has elapsed, the device will extinguish LEDs 48 and 49 and illuminate LED 47. Audio prompt 126 (stand clear, analyzing rhythm) will also be issued and a new sequence of up to three ECG analyses/shocks will begin.

If the caregiver detects circulation during step 132, the caregiver may turn off the defibrillator and/or remove the electrodes. Alternatively, the caregiver may not perform further CPR, but nonetheless allow the device to reanalyze the ECG after each one minute CPR period in order to provide repeated periodic monitoring to ensure the patient continues to have a non-shockable rhythm.

Thus, in the continuing presence of a shockable rhythm, the sequence of three ECG analyses and three shocks, followed by one minute of CPR, will continue indefinitely. If, instead, a non-shockable rhythm is or becomes present, the sequence will be analyze/no shock advised, one minute of CPR, analyze/no shock advised, one minute of CPR, etc. When a shock is effective in converting the patient's heart rhythm to a heart rhythm that does not require further defibrillating treatment, the sequence will be: analyze/shock advised, shock (saves patient), analyze/no shock advised, one minute CPR period (if pulse is detected then caregiver will not do CPR during this period), analyze/no shock advised, one minute CPR period, etc., continuing until the caregiver turns the defibrillator (e.g., if the caregiver detects a pulse) or the electrodes are removed.

Figure 14:
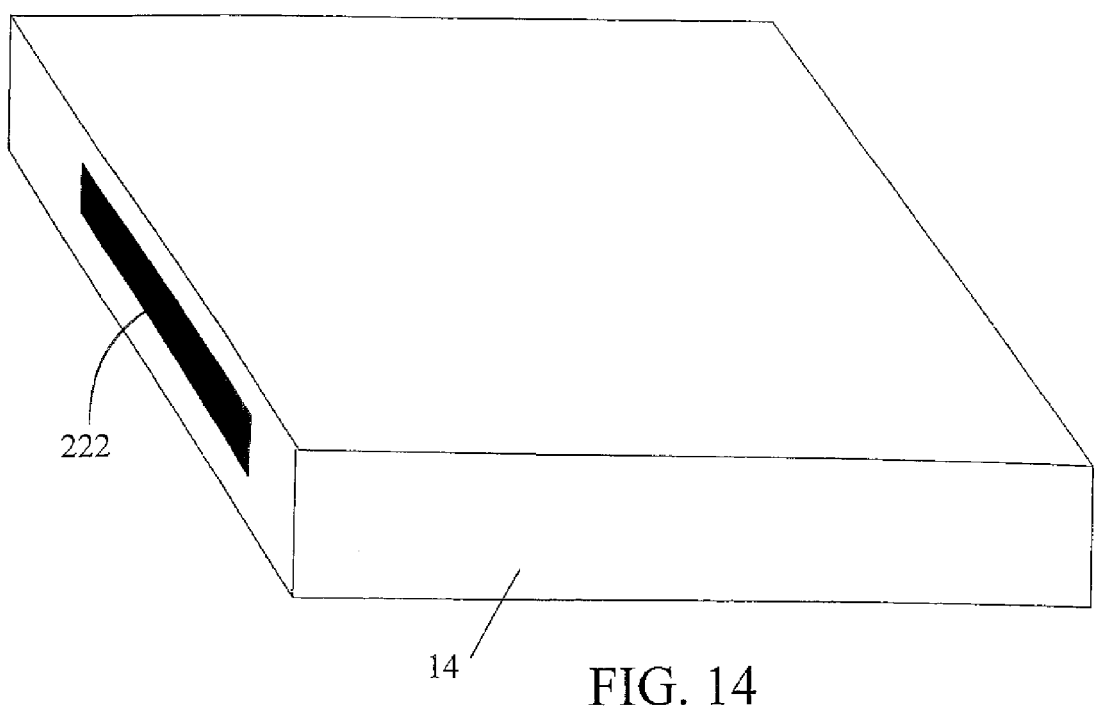
FIG. 14 is an isometric view of an electrode well along one side of the housing.
Figure 15:
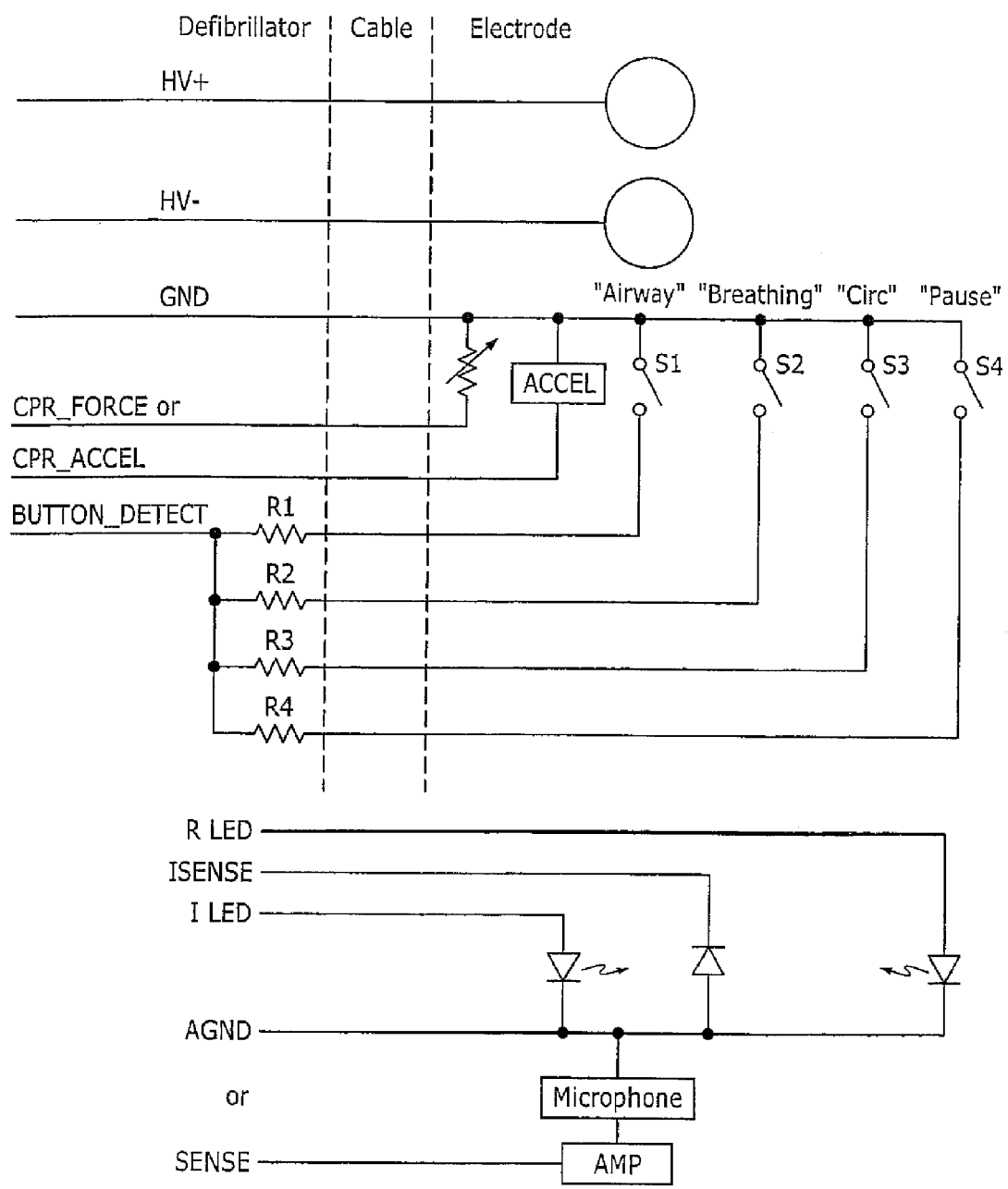
FIG. 15 is a schematic of the electronics contained in the integrated electrode pad of FIG. 12.

If electrode contact is lost at any time (as determined by the impedance data received from the electrode assembly), this will result in an appropriate audio prompt, such as "check electrodes" and illumination of the LED adjacent graphic 46. The electrodes 208 may be stored in a well 222 (FIG. 14) that is structurally integrated with the housing 14 or may be a separate pouch 16.

It has also been discovered that a not-insignificant portion of caregivers are unable to open the packaging for the electrodes; therefore, a sensor may be provided to determine if the electrode package has been opened. If detection of the electrode package 16 opening has not occurred within a predetermined period of time, the unit will provide more detailed instructions to assist the user in opening the packaging 16.

Figure 12:
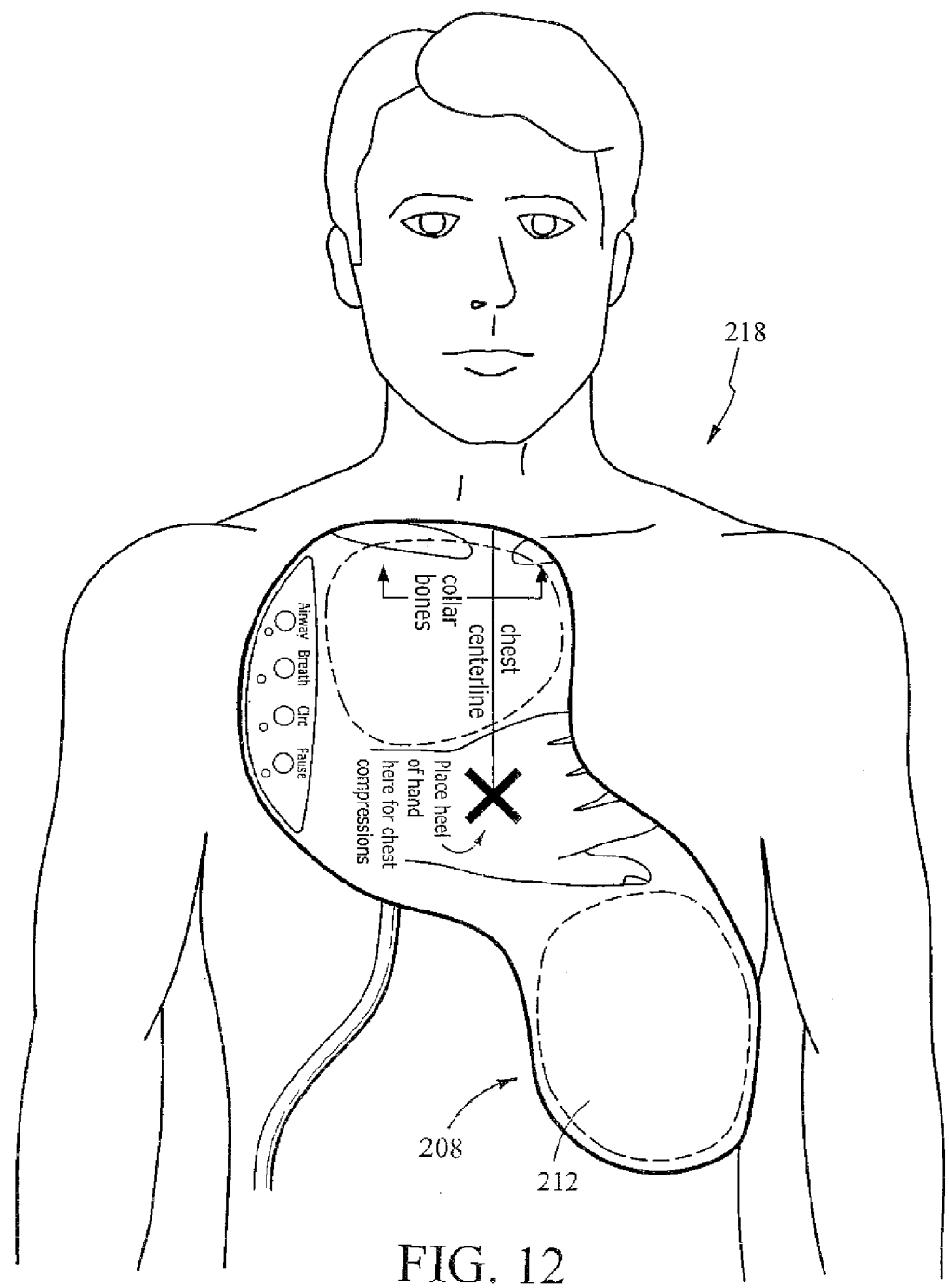
FIG. 12 shows an integrated electrode pad.
Figure 13:
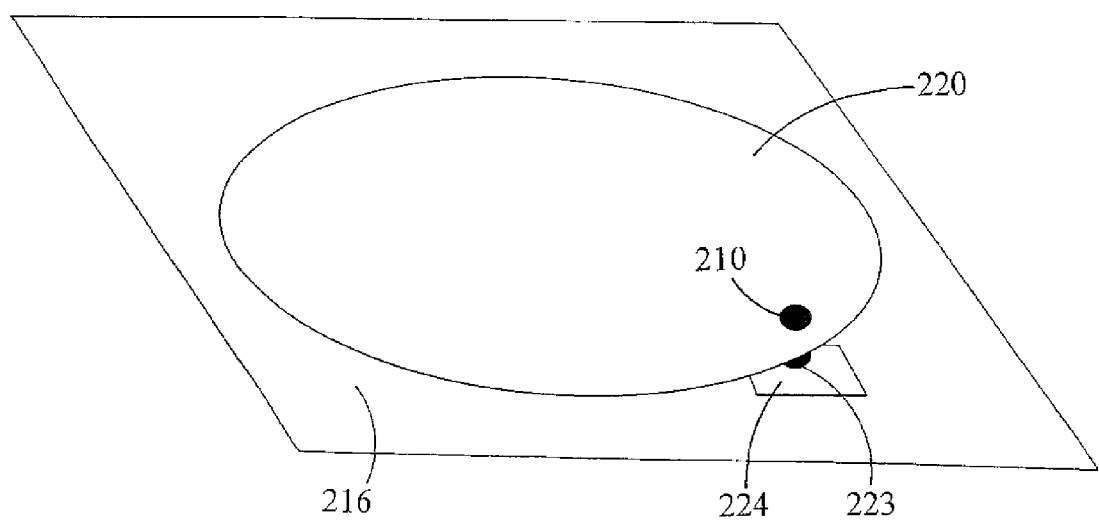
FIG. 13 is another view of an electrode pad.

Referring to FIGS. 12 and 13, in preferred implementations, a means is provided of detecting and differentiating successful completion of multiple steps of electrode application: (1) taking the electrodes 208 out of the storage area 222 or pouch 16; (2) peeling the left pad 212 from the liner 216; (3) peeling the right pad 214 from the liner 216; (4) applying the left pad 212 to the patient 218; and (5) applying the right pad 214 to the patient 218. Referring to FIGS. 12 and 13, a package photosensor 210 is provided on the outer face of the electrode backing 220. Detection that the electrode 208 is sealed in the storage area is determined by the photosensor output being below a threshold. A photoemitter/photosensor (PEPS) 223 combination is embedded into each electrode facing towards the liners 216. The liner 216 is constructed so that a highly reflective aluminized Mylar, self-adhesive disk 224 is applied to the liner 216 in the location directly beneath the PEPS 223. The reflective disk 224 is coated with a silicone release material on the side in contact with the electrode 208 so that it remains in place when the electrode 208 is removed from the liner. In such a configuration, the processor is fully capable of differentiating substantially the exact step in the protocol related to electrode application. When the package photosensor 210 detects light above a certain threshold, it is known that the electrodes have been removed from the storage area 222 or pouch 16. The high reflectance area 224 beneath each PEPS 223 provides a signal that is both a high intensity as well as being synchronous with the emitter drive with low background level; thus it is possible to distinguish with a high degree of accuracy which, if either, of the electrodes 212, 214 is still applied to the liner 216. When an electrode 212, 214 is removed from the liner 216 the background level of the signal increases due to ambient light while the synchronous portion decreases because there is little if any of the photoemitter light reflected back into the photosensor; this condition describes when an electrode 212, 214 is removed from the liner 216. When it has been determined that an electrode 212, 214 has been removed from the liner 216, the processor means 20 proceeds to the next state—looking for application of that electrode to the patient. Application of the electrode 212, 214 to the patient will result in a decrease in the background level of the signal output and some synchronous output level intermediate to the synchronous level measured when the electrode 212, 214 was still on the liner 216. If it has been determined that both electrodes 212, 214 are applied to the patient 218 but there is an impedance measured between the electrodes that is significantly outside the normal physiological range then it is very possible that the user has applied the electrodes to the patient without removing the patient's shirt. Surprisingly, this is not uncommon in real situations with users; a patient's shirt will have been only partially removed when electrodes are applied resulting in insufficient electrical contact with the patient's skin. FIG. 6d shows the flowchart for prompting related to retrieval and application of electrodes. As in the case with responding to a user's interactions.

Many other implementations are within the scope of the following claims.

For example, the graphics on the center decal can be accompanied by any desired light source. For instance, if desired, all of the graphics can be translucent, and can be backlit. Alternatively, the graphics can be provided in the form of LED images, rather than on a decal.

While the electrodes have been illustrated in the form of an integral electrode assembly, separate electrodes may be used.

In some implementations, generally all of the graphically illustrated steps are shown at the same time, e.g., as illustrated by the decal described above. This arrangement allows the caregiver to see the steps that will be performed next and thus anticipate the next step and begin it early if possible. However, alternatively, the graphics can be displayed one at a time, e.g., by using a screen that displays one graphic at a time or backlit graphics that are unreadable when not back lit. This arrangement may in some cases avoid overwhelming novice or lay rescuers, because it does not present the caregiver with too much information all at the same time.

If desired, each graphic could have an associated button that, when pressed, causes more detailed audio prompts related to that graphic to be output by the defibrillator.

Figure 11:
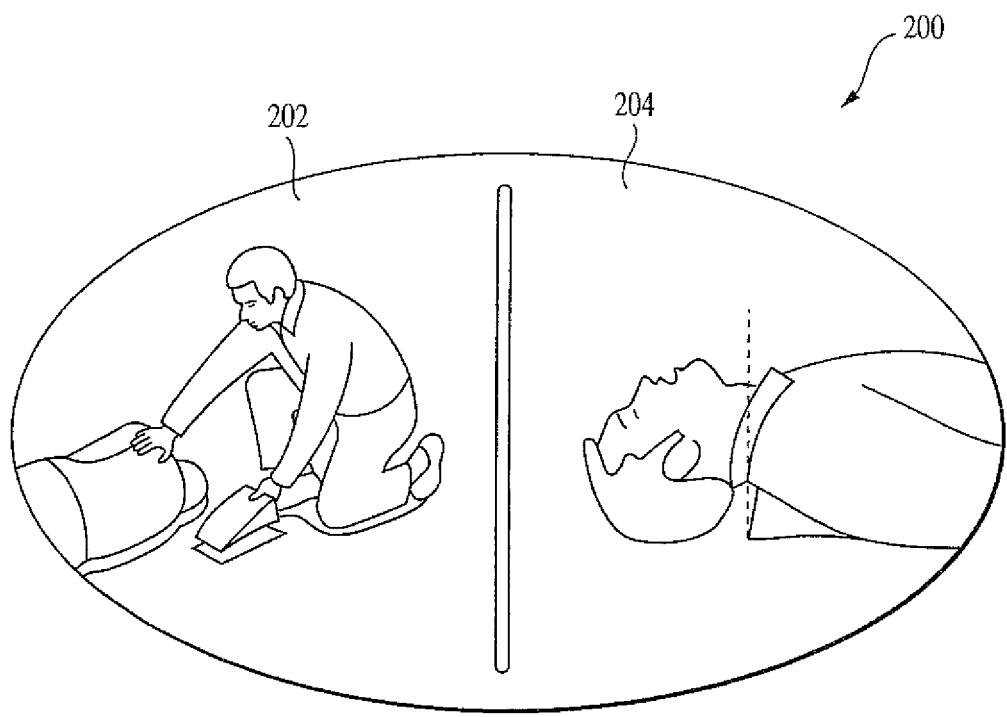
FIG. 11 is a plan view of a decal providing graphical instructions on the cover for placing the cover under a patient's shoulders.

The cover 12 of the AED may include a decal on its underside, e.g., decal 200 shown in FIG. 11. Decal 200 illustrates the use of the cover as a passive airway support device, to keep the patient's airway open during resuscitation. Graphic 202 prompts the caregiver to roll the patient over and place cover 12 under the patient's shoulders, and graphic 204 illustrates the proper positioning of the cover 12 under the patient to ensure an open airway.

Figure 5:
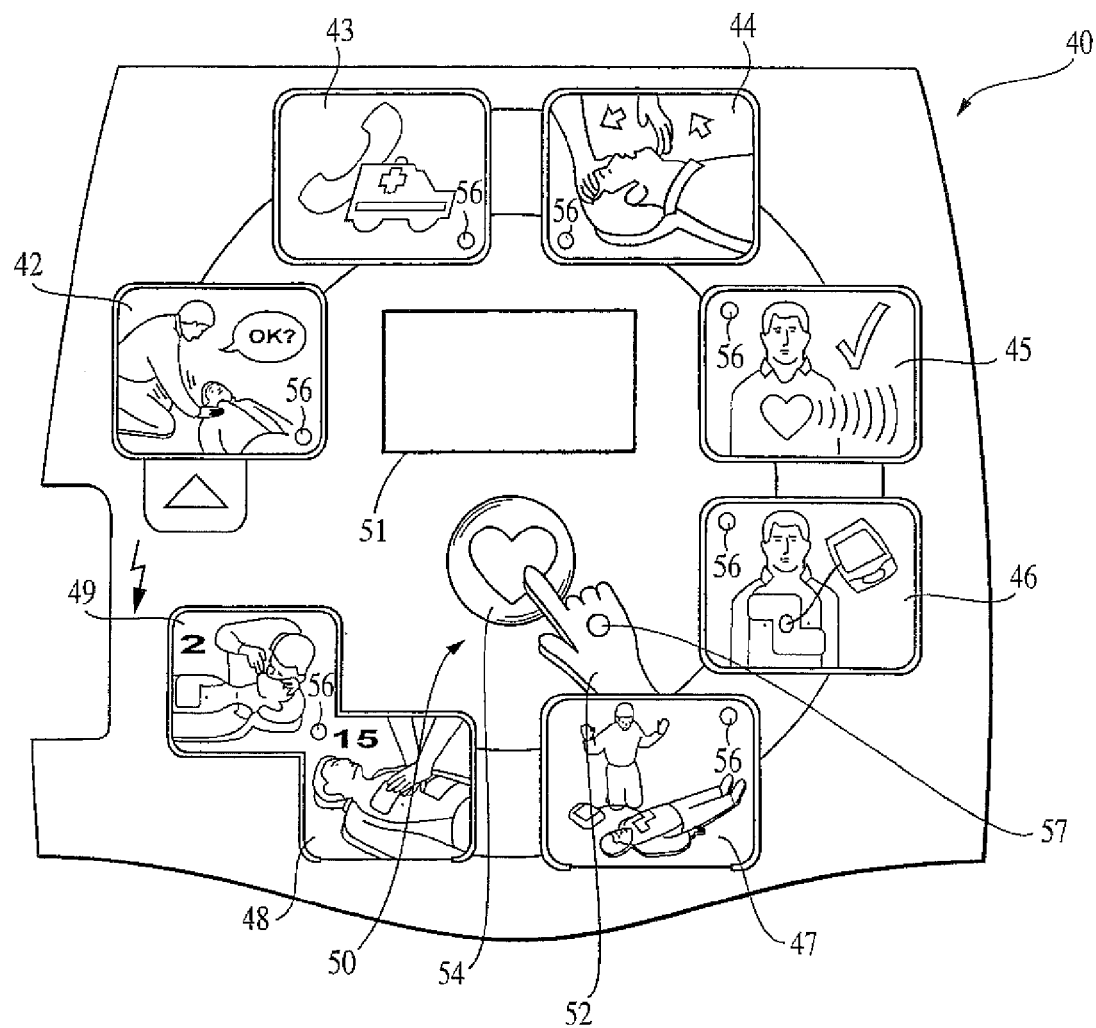
FIG. 5 is a plan view of the graphical interface decal used on the device housing of the AED of FIG. 1, as shown in FIG. 2.

While such a graphic is not included in the decal shown in FIG. 5, the decal 40 may include a graphic that would prompt the user to check to see if the patient is breathing. Such a graphic may include, e.g., a picture of the caregiver with his ear next to the patient's mouth. The graphic may also include lines indicating flow of air from the patient's mouth.

"Illuminated", "light up", and similar terms are used herein to refer to both a steady light and a light of varying intensity (e.g., blinking). A blinking light may be used, if desired, to more clearly draw the user's attention to the associated graphic.

Figure 16:
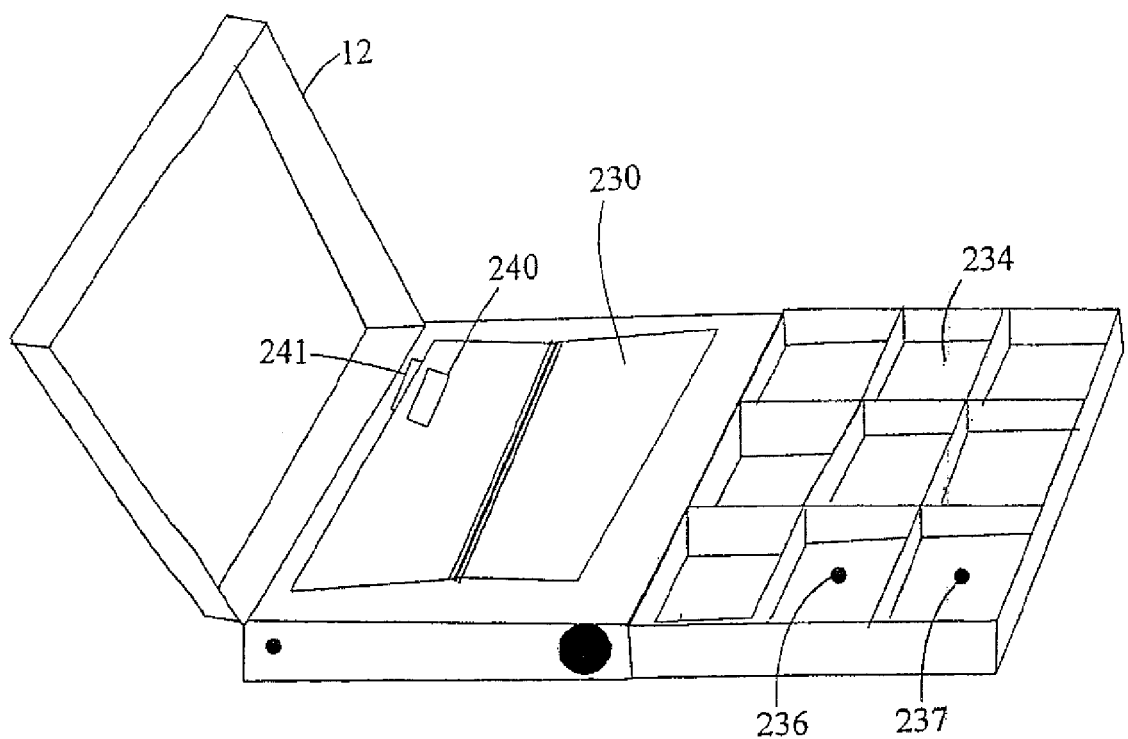
FIG. 16 is an isometric view of a first-aid kit implementation.

Referring to FIG. 16, in other implementations, a home first aid device may be provided for providing instructions and therapy, as needed, for a variety of medical situations. In some implementations, the device would include: (a) a cover to the device whose removal the processor is capable of detecting; (b) a series of bound pages 230 on the face of the device under the cover 12 with a detection means providing for determining to which page the bound pages have been turned; (c) a processor; (d) a speaker 232 providing audio output. The home first aid device may also include a portion of the device used specifically for storage of items commonly used in the course of providing aid such as bandaids, bandages, splints, antiseptic, etc. The storage area preferably takes the form of a partitioned tray 234. Alternatively, the storage area may take the form of multiple pockets, pouches, straps, or slots. The storage area is partitioned into individual wells in which each of the items is stored. Photoelectric sensors 236, 237 may be provided in each of the wells, thereby providing a means of determining which, if any, of the items has been removed by the user. Detecting which page the bound pages are turned to may be provided by embedding small high magnetic intensity samarium cobalt magnets 240 in locations specific to each page. In some implementations, the magnets 240 are located along the bound edge of the pages, outside the printed area of the pages. Magnetic sensors 241 are located in the device housing 14 that correspond to the locations where the magnets 240 located in the specific pages make contact when the specific page is turned. The magnetic sensor 241 may be a semiconductor device employing the Hall effect principle, but may also be a reed switch or other magnetically activated switch. By providing a means of detecting user actions automatically such as the detection of which page the user has turned to or which first aid item has been removed from the storage container, the device is able to interact and respond to the rescuer in an invisible manner, improving both speed as well as compliance to instructions. In such a manner, interactivity is preserved while at the same time providing a printed graphical interface to the user.

What is claimed is:

1. A cardiac resuscitation system for assisting a caregiver in delivering electrical resuscitation therapy to a patient using disposable therapy electrodes that are stored in packaging and removed and applied to the skin of the patient's thorax, the system comprising
    a user interface configured to deliver prompts to a caregiver to assist the caregiver in delivering electrical resuscitation therapy to a patient;
    at least one photoelectric sensor configured to detect the caregiver's progress in removing a therapy electrode from its packaging and applying it to the patient;
    a memory in which a plurality of different prompts are stored;
    a processor configured to determine which of the different prompts should be selected for delivery based on the progress detected by the sensor.

2. The system of claim 1 wherein there are a plurality of photosensors configured to detect the caregiver's progress in delivering the therapy, including at least one photosensor on each electrode.

3. The system of claim 1 wherein the processor is configured to vary the time at which prompts are delivered based on the progress detected by the sensor.

4. The system of claim 1 further comprising one or more additional sensors in electrical contact with the body and configured to detect the caregiver's progress in delivering the therapy.

5. The system of claim 2 wherein the photosensor on each electrode comprises a photoemitter/photosensor.

6. The system of claim 5 in which a reflective surface is provided on the interior of the electrode packaging in the vicinity of each of the photosensors when each electrode is in the position in which it is stored in the packaging, wherein the reflective surface reflects light emitted by the photoemitter and the reflected light is sensed by the photosensor.

7. The system of claim 6 in which the processor determines that the packaging has been opened based on an increase in sensed light.

8. The system of claim 6 in which the processor determines that an electrode has been peeled from a liner to which it was attached in the packaging by recognizing a reduction in reflected photoemitter light sensed at the photosensor.

9. The system of claim 5 in which the processor determines that the packaging has been opened based on an increase in sensed light.

10. The system of claim 5 in which the processor determines that an electrode is still in an unopened package by determining that the light level sensed by the photosensor on the electrode is below a threshold.

11. The system of claim 1 in which the photosensor and processor are configured to detect whether the electrode has been applied to clothing rather than to skin.

12. The system of claim 11 in which detection of an intermediate level of reflected photoemitter light is used by the processor to determine that the electrode has been applied to a surface.

13. The system of claim 12 in which detection of whether the surface to which the electrode is applied is skin or clothing is accomplished using sensors that measure impedance between the two electrodes.

14. The system of claim 1 wherein the processor is configured to slow down the rate at which prompts are delivered when progress is slower than a predetermined pace.

15. The system of claim 1 wherein the progress detected by the sensors comprises whether a step in the protocol has been initiated and whether the step has been completed.

16. The system of claim 1 wherein the user interface delivers at least some of the prompts as oral instructions to be heard by the caregiver.

17. The system of claim 1 wherein the user interface delivers at least some of the prompts as visual instructions to be seen by the caregiver.

18. The system of claim 17 wherein the user interface comprises an electronic display.

19. The system of claim 17 wherein the electronic display provides a series of images.

* * * * *